United States Patent
Lee et al.

(10) Patent No.: US 7,678,061 B2
(45) Date of Patent: Mar. 16, 2010

(54) SYSTEM AND METHOD FOR CHARACTERIZING PATIENT RESPIRATION

(75) Inventors: Kent Lee, Fridley, MN (US); Quan Ni, Shoreview, MN (US); Jesse W. Hartley, Lino Lakes, MN (US); John D. Hatlestad, Maplewood, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1350 days.

(21) Appl. No.: 10/824,941

(22) Filed: Apr. 15, 2004

(65) Prior Publication Data

US 2005/0065447 A1 Mar. 24, 2005

Related U.S. Application Data

(60) Provisional application No. 60/504,228, filed on Sep. 18, 2003.

(51) Int. Cl.
*A61B 5/08* (2006.01)
*A61N 1/00* (2006.01)
(52) U.S. Cl. ........................ 600/529; 600/538
(58) Field of Classification Search ............. 600/484, 600/534, 536, 529, 513
See application file for complete search history.

(56) References Cited

U.S. PATENT DOCUMENTS

| 4,365,636 | A | 12/1982 | Barker |
| 4,562,841 | A | 1/1986 | Brockway et al. |
| 4,827,935 | A | 5/1989 | Geddes et al. |
| 4,928,688 | A | 5/1990 | Mower |
| 5,036,849 | A | 8/1991 | Hauck et al. |
| 5,105,354 | A * | 4/1992 | Nishimura ............ 600/484 |
| 5,146,918 | A | 9/1992 | Kallok et al. |
| 5,178,156 | A | 1/1993 | Takishima et al. |
| 5,187,657 | A | 2/1993 | Forbes |
| 5,203,348 | A | 4/1993 | Dahl et al. |
| 5,230,337 | A | 7/1993 | Dahl et al. |
| 5,233,983 | A | 8/1993 | Markowitz |
| 5,284,136 | A | 2/1994 | Hauck et al. |

(Continued)

FOREIGN PATENT DOCUMENTS

EP  0 940 155 A  9/1999

(Continued)

OTHER PUBLICATIONS

Olusola et al., *Nightcap: Laboratory and home-based evaluation of a portable sleep monitor*, 32 Psychophysiology, 32-98 (1995). Abstract only.

(Continued)

*Primary Examiner*—Patricia C Mallari
(74) *Attorney, Agent, or Firm*—Hollingsworth & Funk, LLC

(57) ABSTRACT

Patient respiration may be characterized using a marked respiration waveform involving a respiration waveform annotated with symbols, markers or other indicators representing one or more respiration characteristics. A respiration waveform may be acquired by sensing a physiological parameter modulated by respiration. A marked respiration waveform may be generated based on the acquired respiration waveform and one or more detected respiration waveform characteristics and/or respiration-related conditions. One or more components used to generate the marked respiratory waveform may be fully or partially implantable.

15 Claims, 20 Drawing Sheets

U.S. PATENT DOCUMENTS

| | | | |
|---|---|---|---|
| 5,301,677 A | 4/1994 | Hsung | |
| 5,313,953 A | 5/1994 | Yomtov et al. | |
| 5,334,222 A | 8/1994 | Salo et al. | |
| 5,335,657 A | 8/1994 | Terry, Jr. et al. | |
| 5,348,008 A * | 9/1994 | Bornn et al. | 600/301 |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,485,851 A * | 1/1996 | Erickson | 600/529 |
| 5,540,727 A | 7/1996 | Tockman et al. | |
| 5,540,732 A * | 7/1996 | Testerman | 607/42 |
| 5,545,186 A | 8/1996 | Olson et al. | |
| 5,545,202 A | 8/1996 | Dahl et al. | |
| 5,549,655 A * | 8/1996 | Erickson | 607/42 |
| 5,603,732 A | 2/1997 | Dahl et al. | |
| 5,738,102 A | 4/1998 | Lemelson | |
| 5,814,087 A | 9/1998 | Renirie | |
| 5,836,987 A | 11/1998 | Baumann et al. | |
| 5,855,593 A | 1/1999 | Olson et al. | |
| 5,860,918 A * | 1/1999 | Schradi et al. | 600/300 |
| 5,861,011 A | 1/1999 | Stoop | |
| 5,876,353 A * | 3/1999 | Riff | 600/547 |
| 5,916,243 A | 6/1999 | KenKnight et al. | |
| 5,944,680 A | 8/1999 | Christopherson et al. | |
| 5,964,778 A | 10/1999 | Fugoso et al. | |
| 5,974,340 A * | 10/1999 | Kadhiresan | 607/18 |
| 6,026,320 A | 2/2000 | Carlson et al. | |
| 6,044,298 A | 3/2000 | Salo et al. | |
| 6,045,513 A | 4/2000 | Stone et al. | |
| 6,055,454 A | 4/2000 | Heemels | |
| 6,064,910 A * | 5/2000 | Andersson et al. | 607/20 |
| 6,076,015 A | 6/2000 | Hartley et al. | |
| 6,091,973 A | 7/2000 | Colla et al. | |
| 6,120,441 A * | 9/2000 | Griebel | 600/300 |
| 6,126,608 A * | 10/2000 | Kemme et al. | 600/459 |
| 6,126,611 A | 10/2000 | Bourgeois et al. | |
| 6,128,534 A | 10/2000 | Park et al. | |
| 6,132,384 A * | 10/2000 | Christopherson et al. | 600/529 |
| 6,141,581 A | 10/2000 | Olson et al. | |
| 6,190,326 B1 | 2/2001 | McKinnon et al. | |
| 6,213,942 B1 * | 4/2001 | Flach et al. | 600/300 |
| 6,221,011 B1 | 4/2001 | Bardy | |
| 6,251,126 B1 * | 6/2001 | Ottenhoff et al. | 607/42 |
| 6,258,039 B1 | 7/2001 | Okamoto et al. | |
| 6,259,947 B1 | 7/2001 | Olson et al. | |
| 6,270,457 B1 | 8/2001 | Bardy | |
| 6,272,377 B1 | 8/2001 | Sweeney et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,351,669 B1 | 2/2002 | Harley et al. | |
| 6,353,759 B1 | 3/2002 | Harley et al. | |
| 6,358,203 B2 | 3/2002 | Bardy | |
| 6,363,270 B1 | 3/2002 | Colla et al. | |
| 6,368,284 B1 | 4/2002 | Bardy | |
| 6,368,287 B1 | 4/2002 | Hadas | |
| 6,371,922 B1 | 4/2002 | Baumann et al. | |
| 6,375,621 B1 | 4/2002 | Sullivan | |
| 6,398,728 B1 | 6/2002 | Bardy | |
| 6,411,848 B2 | 6/2002 | Kramer et al. | |
| 6,415,183 B1 * | 7/2002 | Scheiner et al. | 607/42 |
| 6,424,865 B1 | 7/2002 | Ding | |
| 6,438,410 B2 | 8/2002 | Hsu et al. | |
| 6,440,066 B1 | 8/2002 | Bardy | |
| 6,449,503 B1 | 9/2002 | Hsu | |
| 6,459,929 B1 | 10/2002 | Hopper et al. | |
| 6,480,733 B1 | 11/2002 | Turcott | |
| 6,487,443 B2 | 11/2002 | Olson et al. | |
| 6,542,775 B2 | 4/2003 | Ding et al. | |
| 6,574,507 B1 | 6/2003 | Bonnet | |
| 6,589,188 B1 | 7/2003 | Street et al. | |
| 6,597,951 B2 | 7/2003 | Kramer et al. | |
| 6,600,949 B1 * | 7/2003 | Turcott | 600/518 |
| 6,641,542 B2 * | 11/2003 | Cho et al. | 600/529 |
| 6,773,404 B2 | 8/2004 | Poezevera et al. | |
| 6,830,548 B2 * | 12/2004 | Bonnet et al. | 600/529 |
| 6,881,192 B1 * | 4/2005 | Park | 600/529 |
| 6,890,306 B2 * | 5/2005 | Poezevera | 600/533 |
| 6,904,320 B2 * | 6/2005 | Park et al. | 607/17 |
| 6,928,324 B2 * | 8/2005 | Park et al. | 607/20 |
| 7,081,095 B2 * | 7/2006 | Lynn et al. | 600/538 |
| 2002/0193697 A1 * | 12/2002 | Cho et al. | 600/529 |
| 2002/0193839 A1 * | 12/2002 | Cho et al. | 607/17 |
| 2003/0023184 A1 | 1/2003 | Pitts-Crick et al. | |
| 2003/0055461 A1 | 3/2003 | Girouard et al. | |
| 2003/0100925 A1 | 5/2003 | Pape et al. | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0195571 A1 * | 10/2003 | Burnes et al. | 607/9 |
| 2003/0199945 A1 | 10/2003 | Ciulla | |
| 2003/0204213 A1 | 10/2003 | Jensen et al. | |
| 2004/0002742 A1 | 1/2004 | Florio | |
| 2004/0088027 A1 | 5/2004 | Burnes et al. | |
| 2004/0102814 A1 * | 5/2004 | Sorensen et al. | 607/17 |
| 2004/0138719 A1 | 7/2004 | Cho et al. | |
| 2004/0210261 A1 * | 10/2004 | King et al. | 607/9 |
| 2005/0043652 A1 * | 2/2005 | Lovett et al. | 600/595 |
| 2005/0119711 A1 * | 6/2005 | Cho et al. | 607/42 |

FOREIGN PATENT DOCUMENTS

| | | |
|---|---|---|
| EP | 1 151 718 A | 11/2001 |
| WO | 99/04841 | 2/1999 |
| WO | WO 00/01438 A | 1/2000 |
| WO | WO 00/17615 | 3/2000 |
| WO | 02/087696 | 7/2002 |

OTHER PUBLICATIONS

Verrier et al., *Sleep, dreams, and sudden death: the case for sleep as an autonomic stress test for the heart*, 31 Cardiovascular Research 181-211 (1996).

Verrier et al., *Sleep Related Cardiovascular Risk: New Home-Based Monitoring Technology for Improved Diagnosis and Therapy*, 2 A.N.E. 158-175 (1997).

Waldemark et al., *Detection of Apnea using Short Window FFT Technique and Artificial Neural Network*, 3390 SPIE International Society for Optical Engineering 122-133 (1998). (partial article).

Medtronic, KAPPA® 400 Series and DX2 Pacemakers, Model 9952, vol. II, Pacemaker Reference Guide, 2001, selected pages (10 total).

* cited by examiner

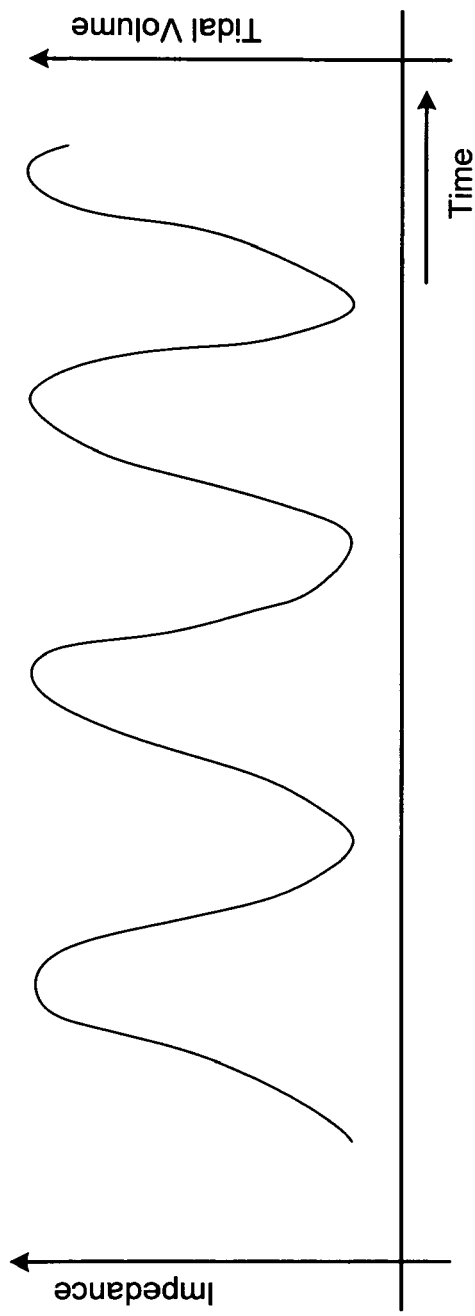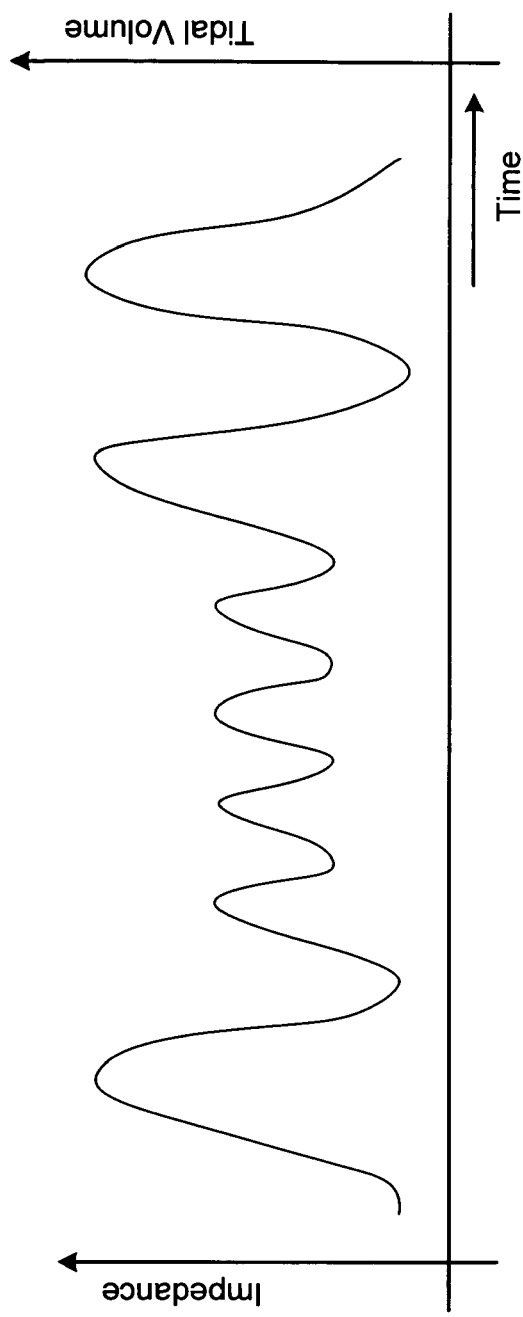

US 7,678,061 B2

SYSTEM AND METHOD FOR CHARACTERIZING PATIENT RESPIRATION

RELATED PATENT DOCUMENTS

This application claims the benefit of Provisional Patent Application Ser. No. 60/504,228, filed on Sep. 18, 2003, to which priority is claimed pursuant to 35 U.S.C. §119(e) and which is hereby incorporated herein by reference.

FIELD OF THE INVENTION

The present invention relates generally to methods and systems for characterizing patient respiration.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other conditions.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker.

Disordered breathing is a respiratory system condition that affects a significant percentage of patients between 30 and 60 years. Disordered breathing, including apnea and hypopnea, may be caused, for example, by an obstructed airway, or by derangement of the signals from the brain controlling respiration. Sleep disordered breathing is particularly prevalent and is associated with excessive daytime sleepiness, systemic hypertension, increased risk of stroke, angina, and myocardial infarction. Disordered breathing can be particularly serious for patients concurrently suffering from cardiovascular deficiencies.

Various types of disordered respiration have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

Because of the complex interactions between the cardiovascular, pulmonary, and other physiological systems, as well as the need for early detection of various respiration diseases and disorders, an effective approach to monitoring and early diagnosis is needed. Accurately characterizing patient respiration aids in monitoring and diagnosing respiration-related diseases or disorders. Evaluating patient respiration information may allow an appropriate therapy to be selected and/or the effectiveness of a delivered therapy to be enhanced.

SUMMARY OF THE INVENTION

Various embodiments of the invention are directed to characterizing respiration using a marked respiration waveform. In accordance with one embodiment, a method for characterizing respiration includes acquiring a respiration waveform. One or more characteristics associated with the patient's respiration are detected. A marked respiration waveform is generated using the respiration waveform and one or more symbols indicating the one or more characteristics associated with the patient respiration. At least one of acquiring the respiration waveform, detecting the one or more characteristics associated with the respiration, and generating the marked respiration waveform is performed at least in part implantably.

Another embodiment of the invention involves a system for characterizing patient respiration. The system includes a respiration waveform sensor configured to acquire a respiration waveform. A respiration processor is configured to determine one or more characteristics associated with the respiration. A waveform generator is coupled to the respiration waveform sensor and the respiration processor. The waveform generator is configured to generate a marked respiration waveform comprising the respiration waveform and symbols indicating the one or more characteristics associated with the respiration. At least one of the respiration waveform sensor, the respiration processor, and the waveform generator includes an implantable component.

BRIEF DESCRIPTION OF THE DRAWINGS

FIGS. 9A and 9B illustrate signals characterizing normal respiration and abnormally shallow respiration utilized in accordance with embodiments of the invention;

Figure 1:
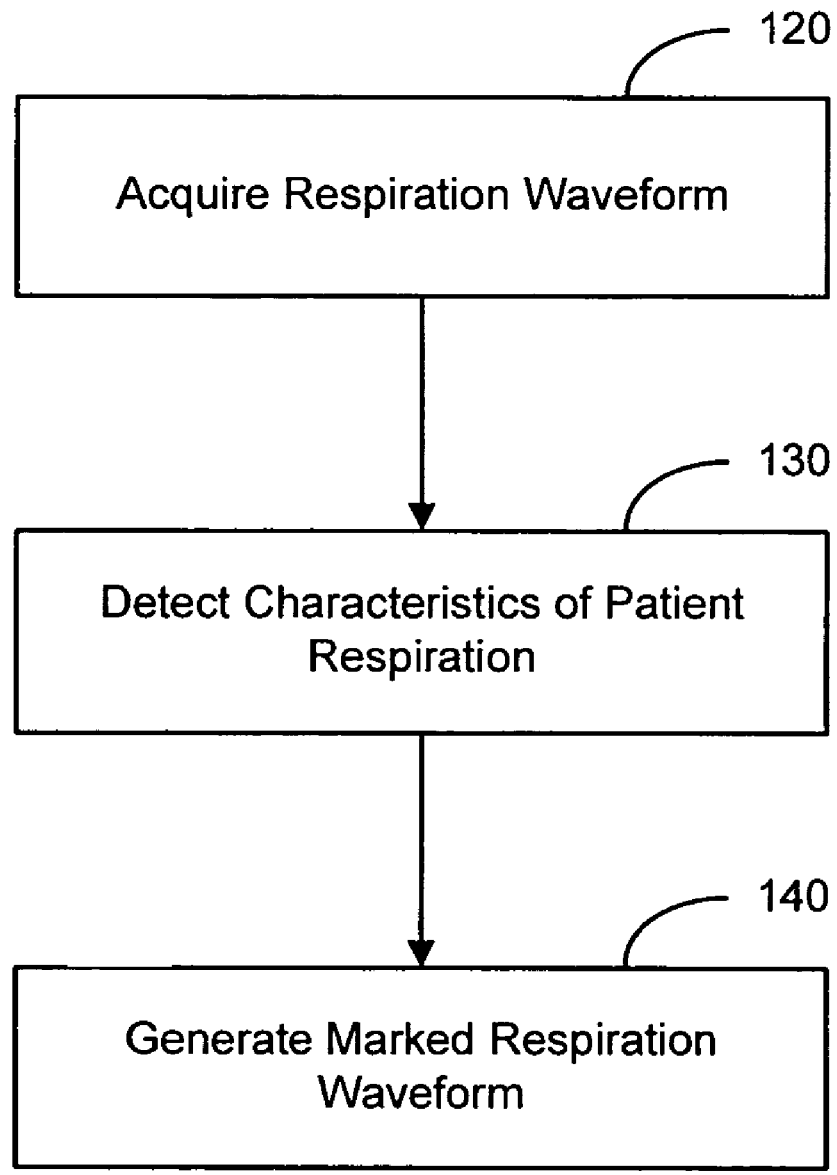
FIG. 1 is a flowchart of a method of characterizing patient respiration by generating a marked respiration waveform accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

Embodiments of the invention involve generating a marked respiration waveform. The marked respiration waveform may characterize a patient's normal respiration, disordered respiration episodes, or other respiration events. For example, a marked respiration waveform representing normal respiration may include a time-based graph of the patient's respiration cycles with symbols indicating various characteristics of the respiration such as rate, tidal volume, minute ventilation, expiration slope, expiration volume, and/or other respiration characteristics or conditions.

If the patient's respiration is abnormal, the marked respiration waveform may include symbols indicating the respiration parameters listed above in addition to symbols further characterizing respiration abnormalities or conditions affecting the respiration. For example, in the case of a disordered breathing episode, the marked respiration waveform may include symbols characterizing the severity, frequency, duration, and/or type of disordered breathing.

Additionally, or alternatively, the marked respiration waveform may include symbols that provide information about one or more conditions affecting the patient's respiration, e.g., pollution index, sleep state, and/or posture. A marked respiration waveform representing the respiration of a patient suffering from a pulmonary disease, for example, may include symbols characterizing various respiration parameters or other conditions associated with the disease, e.g., pulmonary congestion and/or body temperature.

The symbols used to mark the respiration waveform may comprise icons, graphics, alphanumeric characters, or other markers. The symbols may be positioned relative to the respiration waveform to indicate a time of occurrence of the particular parameter indicated by the symbol. A symbol may comprise a icon, graphic, numerical value and/or a textual descriptor associated with a respiration characteristic, e.g., average respiration rate, expiratory slope, etc.

FIG. 1 is a flow chart of a method of generating a marked respiration waveform in accordance with embodiments of the invention. The method involves acquiring 120 a respiration waveform. A respiration waveform may be acquired by sensing a signal modulated by patient respiration, such as airflow or transthoracic impedance, for example. The method further includes detecting 130 one or more characteristics associated with the patient respiration. The one or more characteristics associated with the patient respiration may comprise parameters associated with the respiration waveform morphology and/or a variety of conditions affecting the patient.

In various embodiments, the respiration characteristics may include conditions associated with the respiration, for example, physiological conditions and/or contextual, non-physiological conditions present at the time of the respiration. Physiological conditions may include blood chemistry, expired CO2, patient posture, activity, and/or other conditions. Contextual conditions may involve the ambient environment of the patient, such as ambient humidity, temperature, and/or pollution index, for example.

The respiration characteristics may include parameters of the respiration waveform morphology, including expiration and inspiration slope. The respiration characteristics may include characteristics of the respiration derived from the respiration waveform, e.g., respiration rate, tidal volume, minute ventilation, and breath intervals. Additionally or alternatively, the respiration characteristics may involve symptoms or physiological conditions that may be derived or detected from the respiration waveform, e.g., pulmonary congestion, or disordered breathing episodes. The respiration characteristics may also include parameters characterizing respiration abnormalities, such as the duration, severity, frequency, and/or type of disordered breathing.

The acquired respiration waveform and the detected characteristics of patient respiration may be used to generate 140 a marked respiration waveform. The marked respiration waveform includes the acquired respiration waveform and one or more symbols or other indicators representative of the respiration characteristics. In one implementation, the symbols may be used to indicate discrete portions of the respiration waveform corresponding to the occurrence of the respiration characteristics. In another implementation, the symbols may indicate general respiration conditions or characteristics that pertain globally to a continuous portion the respiration waveform. Various respiration information, including the acquired respiration waveform, information associated with the respiration characteristics, and/or the marked respiration waveform may be stored in memory, transmitted to a separate device, displayed on a computer screen or other type of display, and/or printed for example.

In one implementation, the system for generating a marked respiration waveform may be implantable or include an implantable component. An implantable system for generating a marked respiration waveform may be implemented, for example, as a component of a cardiac device such as a pacemaker, defibrillator, cardiac resynchronizer, implantable cardiac monitor, or other implantable cardiac device.

In another example, the system for generating the marked respiration waveform may be implemented using both patient-internal and patient-external devices operating in coordination. In this example, a first set of components of a marked respiration waveform system may be implemented in one or more patient-internal devices and a second set of components of the marked respiration waveform system may be implemented in one or more patient-external devices. In various configurations, the patient-internal and patient-external devices may communicate through wired or wireless communication links to accomplish marked respiration waveform generation.

Figure 2:
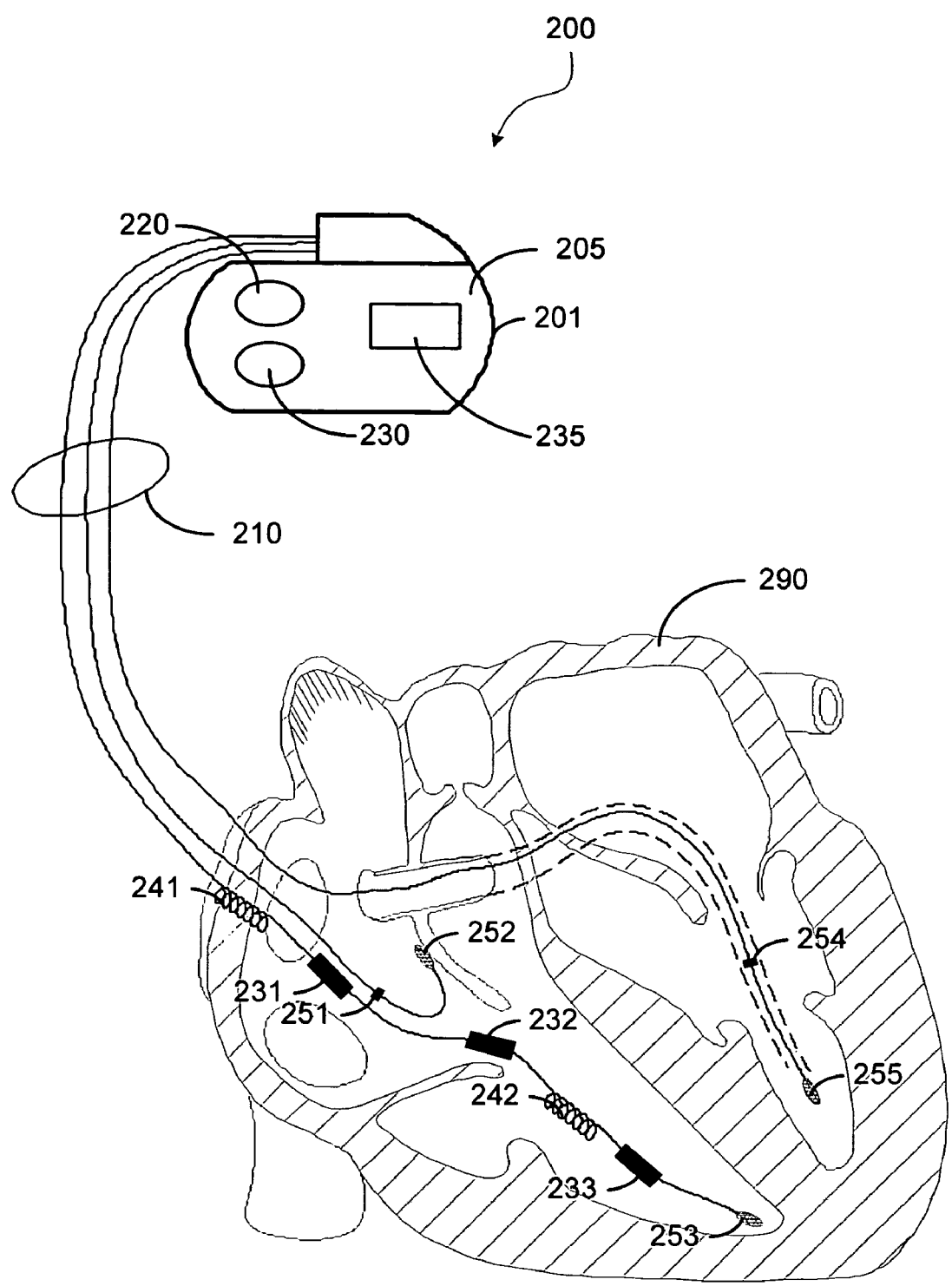
FIG. 2 is a partial view of an implantable device that may include a patient respiration characterization system in accordance with embodiments of the invention.

FIG. 2 is a partial view of an implantable device that includes a system for generating a marked respiration waveform in accordance with embodiments of the invention. In this example, the implantable device comprises a cardiac rhythm management device (CRM) 200 comprising an implantable pulse generator 205 electrically and physically coupled to an intracardiac lead system 210. The marked respiration waveform system may alternatively be implemented in a variety of implantable monitoring, diagnostic, and/or therapeutic devices, such as an implantable cardiac monitoring device, or an implantable drug delivery device, for example.

Portions of the intracardiac lead system 210 are inserted into the patient's heart 290. The intracardiac lead system 210 includes one or more electrodes configured to sense electrical cardiac activity of the heart, deliver electrical stimulation to the heart, and/or to sense the patient's transthoracic impedance. Portions of the housing 201 of the pulse generator 205 may optionally serve as a can electrode.

Communications circuitry is disposed within the housing 201 for facilitating communication between the pulse generator 205 and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors, patient-input devices, and/or information systems.

The pulse generator 205 may optionally incorporate a motion detector 220 that may be used to sense various respiration-related conditions. For example, the motion detector 220 may be configured to sense the patient's activity level and/or the patient's chest wall movements associated with respiratory effort. The motion detector 220 may be implemented as an accelerometer positioned, for example, in or on the housing 201 of the pulse generator 205.

The CRM 200 may incorporate a transthoracic impedance sensor that may be used to acquire the patient's respiration waveform. The transthoracic impedance sensor may include, for example, one or more intracardiac impedance electrodes 231-233 positioned in one or more chambers of the heart 290. The intracardiac impedance electrodes 231-233 may be coupled to impedance drive/sense circuitry 230 positioned within the housing of the pulse generator 205.

In one implementation, impedance drive/sense circuitry 230 generates a current that flows through the tissue between an impedance drive electrode 233 and a can electrode on the housing 201 of the pulse generator 205. The voltage at an impedance sense electrode 231, 232 relative to the can electrode changes as the patient's transthoracic impedance changes. The voltage signal developed between the impedance sense electrode 231, 232 and the can electrode is detected by the impedance sense circuitry 230.

Figure 6:
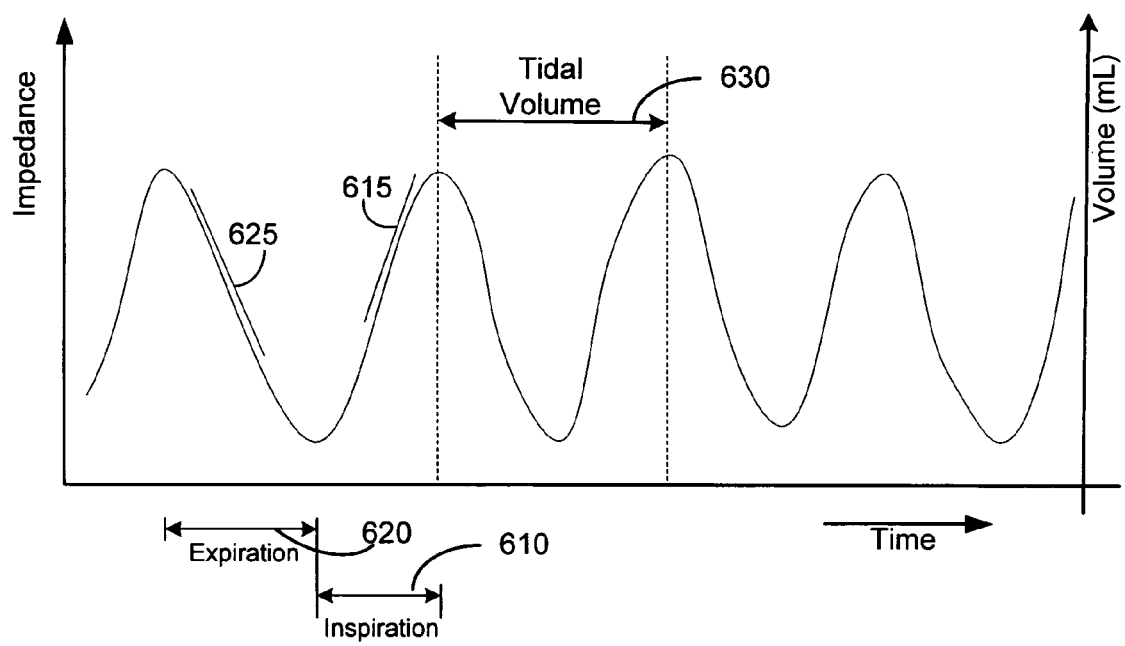
FIG. 6 is a is a graph of a respiration signal generated by a transthoracic impedance sensor that may be used in connection with calculating respiratory characteristics and identifying disordered breathing in accordance with embodiments of the invention.

The voltage signal developed at the impedance sense electrode, 231, 232, illustrated in FIG. 6, is proportional to the patient's transthoracic impedance and represents the patient's respiration waveform. The transthoracic impedance increases during respiratory inspiration 610 yielding a waveform with a positive slope 615. The transthoracic impedance decreases during respiratory expiration 620 yielding a portion of the waveform having a negative slope 625. The peak-to-peak transition 630 of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions, as indicated in FIG. 6.

Returning to FIG. 2, the lead system 210 may include one or more cardiac pace/sense electrodes 251-255 positioned in, on, or about one or more heart chambers for sensing electrical signals from the patient's heart 290 and/or delivering pacing pulses to the heart 290. The intracardiac sense/pace electrodes 251-255, such as those illustrated in FIG. 2, may be used to sense and/or pace one or more chambers of the heart, including the left ventricle, the right ventricle, the left atrium and/or the right atrium. The lead system 210 may include one or more defibrillation electrodes 241, 242 for delivering defibrillation/cardioversion shocks to the heart.

The pulse generator 205 may include circuitry for detecting cardiac arrhythmias and/or for controlling pacing or defibrillation therapy in the form of electrical stimulation pulses or shocks delivered to the heart through the lead system 210. The pulse generator 205 may also include a marked respiration waveform system 235 for generating marked respiratory waveforms in accordance with embodiments of the invention. Although methods for sensing respiration described in this example involve transthoracic impedance measurements, other processes for acquiring a respiration waveform are also possible, including, for example, sensing respiration sounds and/or blood oxygen measurements, among other methods.

Figure 3:
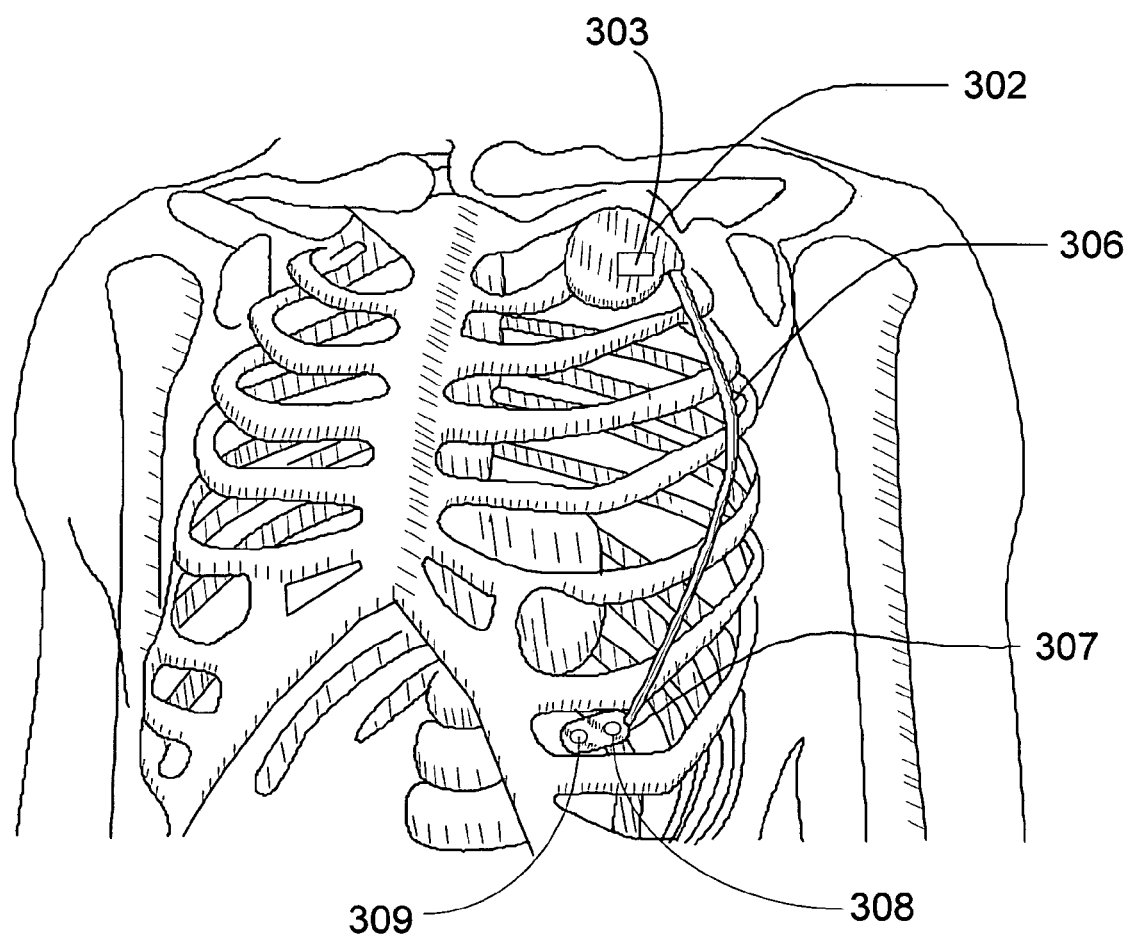
FIG. 3 is a diagram illustrating an implantable transthoracic cardiac device that may be used in connection with characterizing patient respiration in accordance with embodiments of the invention.

FIG. 3 is a diagram illustrating an implantable transthoracic cardiac device that may be used in connection with generating a marked respiration waveform in accordance with embodiments of the invention. The implantable device illustrated in FIG. 3 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Components of the cardiac sensing system, for example, may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent applications Ser. No. 60/462,272, filed Apr. 11, 2003, and Ser. No. 10/462,001, filed Jun. 13, 2003, now U.S. Publication No. 2004/0230229, and Ser. No. 10/465,520, filed Jun. 19, 2003, now U.S. Publication No. 2004/0230230, which are incorporated by reference.

The ITCS device may incorporate circuitry for generating a marked respiration waveform. In one configuration, components of the marked respiration waveform system 303 may be positioned within the primary housing 302 of the ITCS device. A transthoracic impedance sensor used for acquiring a respiration waveform may be implemented using impedance electrodes 308, 309 and/or can electrode coupled to transthoracic impedance circuitry, respiration processor, and waveform generator within the primary housing 302 of the ITCS device.

An impedance sensor may include the impedance drive/sense circuitry coupled to impedance electrodes 308, 309. In one configuration, the impedance drive circuitry generates a current that flows between a subcutaneous impedance drive electrode 308 and a can electrode on the primary housing 302 of the ITCS device. The voltage at a subcutaneous impedance sense electrode 309 relative to the can electrode changes as the patient's transthoracic impedance changes. The voltage signal developed between the impedance sense electrode 309 and the can electrode is sensed by the impedance drive/sense circuitry, producing a respiration waveform such as the respiration waveform depicted in FIG. 6.

As previously discussed, the transthoracic impedance signal is related to patient respiration, with impedance increasing during respiratory inspiration and decreasing during respiratory expiration. Characteristics associated with the respiration may be determined based on respiration waveform morphology or based on other sensed parameters. The marked respiration waveform generator circuitry 303 produces a marked respiration waveform using respiration signals generated by the transthoracic impedance sense circuitry and the determined respiration characteristics.

Communications circuitry is disposed within the housing 302 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

Figure 4:
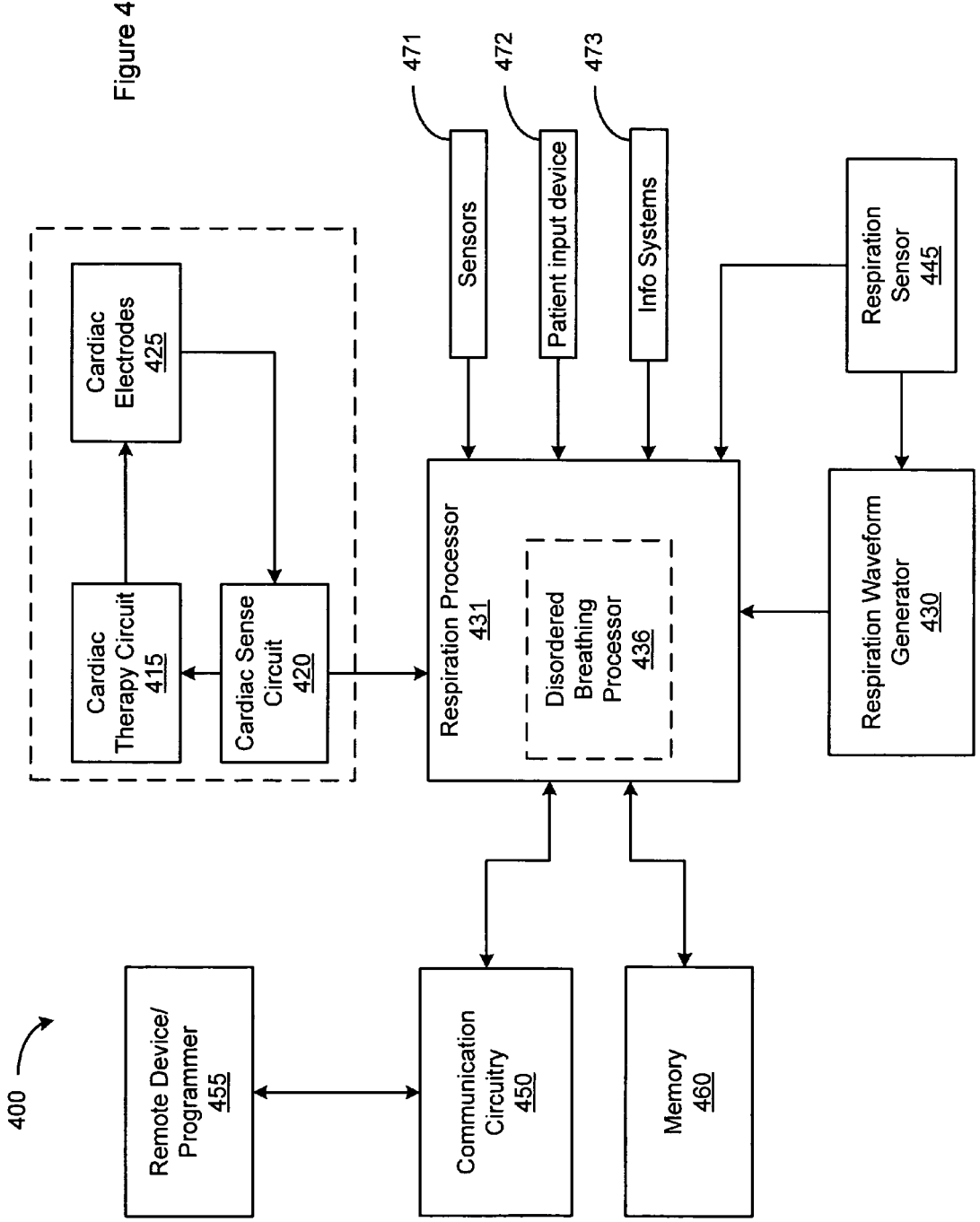
FIG. 4 is a block diagram of a medical system including a cardiac device that may be used to characterize patient respiration in accordance with embodiments of the invention.

FIG. 4 is a block diagram of a medical system 400 including patient-external or fully or partially implantable a medical device 400 incorporating a marked respiration waveform system in accordance with embodiments of the invention. The medical device 400 may optionally include a cardiac therapy circuit 415 and a cardiac sense circuit 420 coupled through a lead system to cardiac electrodes 425. The cardiac electrodes 425, illustrated in FIG. 4 may be used to electrically couple to the patient's heart for sensing electrical cardiac signals and/or delivering therapy to the heart in the form of electrical stimulation energy, e.g., pacing pulses and/or defibrillation/cardioversion shocks as more fully described in connection with FIGS. 2 and 3 above.

The medical system 400 incorporates a system for generating marked respiration waveforms. In the embodiment illustrated in FIG. 4, respiration waveforms are acquired based on signals generated by a respiration sensor 445. In a preferred embodiment, the respiration sensor comprises a transthoracic impedance sensor. Other methods of acquiring a respiration waveform are also possible. Such methods may include, for example, the use of patient-external respiratory bands, respiration flowmeter measurements, implantable or patient-external breath sound detection, blood oxygen levels, and/or other processes.

Various respiration-related conditions affecting the patient may be acquired using the cardiac electrodes 425, sensors 471, patient input devices 472 and/or other information systems 473. The sensors 471 may comprise patient-internal and/or patient-external sensors coupled through leads or wirelessly to the respiration processor 431. The patient input device 472 allows the patient to input information relevant to respiration conditions. For example, the patient input device 472 may be particularly useful for inputting information concerning patient-known information, such as information related to patient smoking, drug use, or other activities or perceptions that are not automatically sensed or detected.

The respiration processor 431 may be coupled to other information systems 473, such as network-connected servers. The respiration processor 431 may access the information systems 473 to acquire information about conditions that may affect patient respiration. In one implementation, the respiration processor 431 accesses the information systems 473 to acquire information about conditions correlated to, or otherwise associated with, an increased or decreased incidence of disordered breathing in the patient. For example, the respiration processor 431 may access an air quality website to acquire the ambient pollution index. In this scenario, a particular level of pollution may be correlated to in increased likelihood of disordered breathing.

Signals from the respiration sensor 445 and/or signals produced by one or more additional sensors or devices 471, 425, 472, 473, may be used by the respiration processor 431 to detect one or more characteristics related to patient respiration. The respiration characteristics are used to generate a marked respiration waveform.

In one embodiment, the respiration characteristics may include parameters associated with the respiration waveform morphology, such as peak inspiration, expiration slope, or inspiration slope. The respiration characteristics may include a variety of physiological and/or non-physiological conditions. For example, the respiration characteristics may include parameters derived from the respiration waveform, e.g., respiration rate, tidal volume, minute ventilation, or breath intervals. Additionally or alternatively, the respiration characteristics may include symptoms and/or physiological conditions derived from the respiration waveform, e.g., dyspnea, pulmonary congestion. The respiration characteristics may include non-physiological, contextual conditions such as pollution, ambient temperature, and/or humidity. The respiration characteristics may also include parameters characterizing disordered breathing, such as duration, severity, frequency, and type of disordered breathing.

In another embodiment, the respiration characteristics may include conditions associated with respiration, including, for example, physiological conditions and/or contextual, non-physiological conditions. Table 1 provides examples of patient conditions that may be used in connection with generation of a marked respiration waveform in accordance with embodiments of the invention. Table 1 also provides illustrative sensing methods that may be employed to sense the conditions. The list provided in Table 1 is not exhaustive and additional or different conditions may be used.

Respiration-related conditions that may be used to generate a marked respiration waveform may include, for example, both physiological and non-physiological (contextual) conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration patterns, blood pressure, among others.

Contextual conditions are non-physiological conditions representing patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. patent application Ser. No. 10/269,611, filed Oct. 11, 2002, now U.S. Pat. No. 7,400,928, which is incorporated by reference herein in its entirety.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer |
| | | | Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | $CO_2$ saturation | Blood analysis |
| | | $O_2$ saturation | |
| | | Blood alcohol content | |
| | | Adrenalin | |
| | | Brain Natriuretic Peptide (BNP) | |

TABLE 1-continued

| Condition Type | | Condition | Sensor type or Detection method |
|---|---|---|---|
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

The respiration processor 431 may optionally include a disordered breathing processor 436 for detecting disordered breathing episodes, including, for example, episodes of central and/or obstructive disordered breathing including apnea, hypopnea, Cheyne-Stokes respiration, or other types of disordered breathing. The disordered breathing processor 436 may also determine various characteristics of the disordered breathing episodes, such as the severity, frequency, duration, and other characteristics of the disordered breathing. The occurrences of disordered breathing and/or disordered breathing characteristics may be indicated in the marked respiration waveform.

Figure 17A:
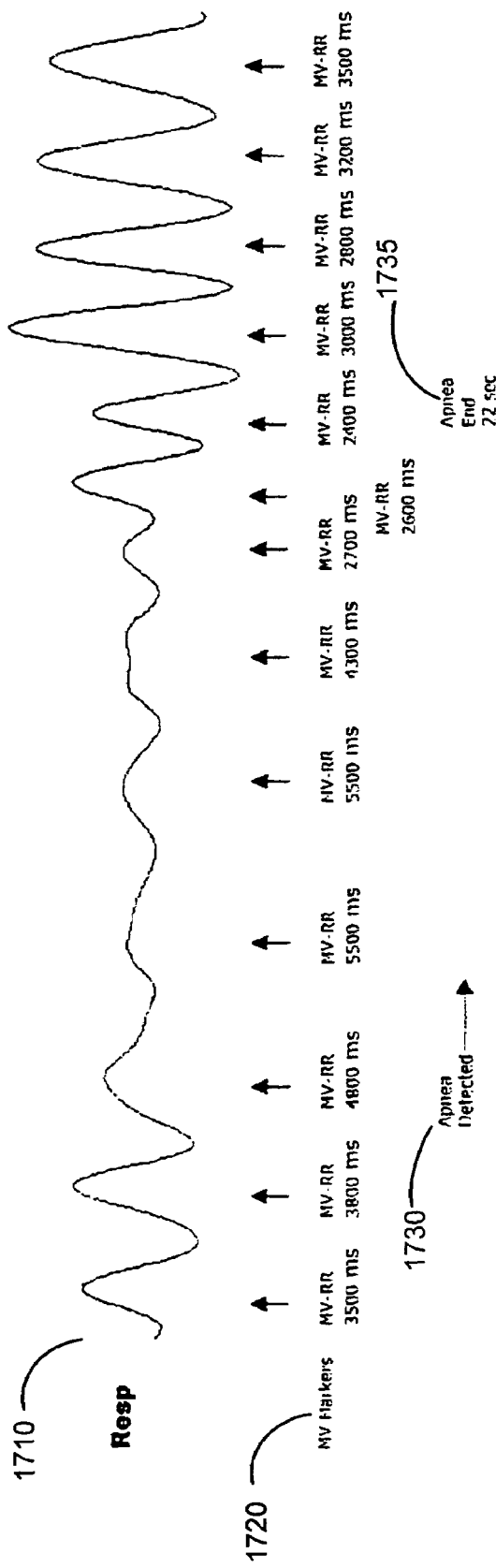
FIG. 17A illustrates a marked respiration waveform in accordance with embodiments of the invention.

The respiration waveform generator 430 uses the acquired respiration waveform, the respiration characteristics derived from the respiration waveform, and/or the other conditions associated with respiration to generate a marked respiration waveform. The marked respiration waveform comprises the respiration waveform and one or more symbols or other indicators associated with the presence of various respiration waveform characteristics and/or respiration-related conditions. As illustrated in FIG. 17A, the symbols may be displayed at positions relative to the marked respiration waveform to indicate the timing of the respiration characteristics and/or conditions.

The medical system 400 may acquire one or more additional waveforms representative of physiological and/or non-physiological conditions affecting the patient. The marked respiration waveform may be displayed along with the one or more additional waveforms. The additional waveforms may be time aligned with the respiration waveform to facilitate comparison, such as the ECG and respiration waveforms depicted in FIG. 17B.

The medical system 400 may include a memory circuit 460 used to store information related to respiration waveforms, including for example, information related to detected respiration characteristics, respiration-related conditions and/or marked or unmarked respiration waveform data. Stored information may be transmitted by communication circuitry 450 to a remote device 455, such as a remote device programmer, a patient management server, or other computing device through a wireless or wired communications link.

Various embodiments described herein may be used within the context of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to submit or acquire patient data or to initiate, terminate or modify therapy.

Methods, structures, or techniques described herein relating to advanced patient management, such as remote patient monitoring, diagnosis, and/or therapy, or other advanced patient management methodologies can incorporate features of one or more of the following references: U.S. Pat. Nos. 6,221,011, 6,270,457, 6,280,380, 6, 312,378, 6,336,903, 6,358,203, 6,368,284, 6,398,728, and 6,440,066 which are incorporated by reference.

Figure 5:
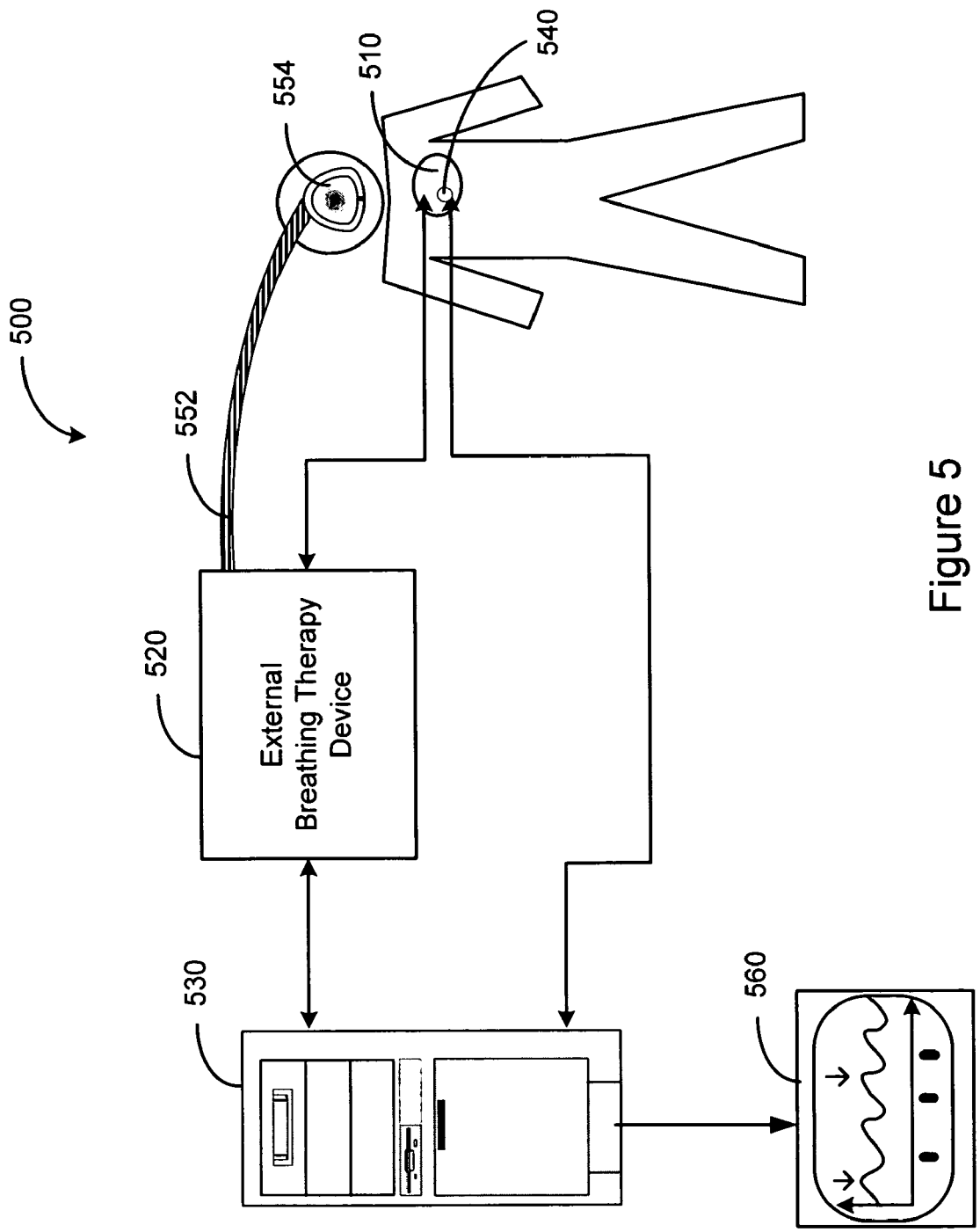
FIG. 5 is a block diagram illustrating a medical system including a patient-internal device that cooperates with a patient-external device to implement patient respiration characterization in accordance with embodiments of the invention.

FIG. 5 is a block diagram illustrating a medical system 500 including a patient-internal device 510 that cooperates with a patient-external device 520 to implement marked respiration waveform generation in accordance with embodiments of the invention. In this example, the marked respiration waveform is displayed on a display device 560.

In one embodiment, the patient-internal device 510 may comprise, for example, an implantable cardiac rhythm management system (CRM) such as a pacemaker, defibrillator, cardiac resynchronizer, or the like. The patient-external device 520 may comprise, for example, an external breathing therapy device such as a continuous positive airway pressure device (CPAP), bi-level positive airway pressure device (bi-PAP) or other positive airway pressure device, generically referred to herein as xPAP devices.

An xPAP device 520 develops a positive air pressure that is delivered to the patient's airway through tubing 552 and mask 554 connected to the xPAP device 520. Positive airway pressure devices are often used to treat disordered breathing. In one configuration, for example, the positive airway pressure provided by the xPAP device 520 acts as a pneumatic splint keeping the patient's airway open, thus reducing the severity and/or number of occurrences of disordered breathing due to airway obstruction. In addition to delivering breathing therapy, the xPAP device 520 may provide a number of monitoring and/or diagnostic functions in relation to the respiratory system. For example, the xPAP device 520 may sense respiration, using an oxygen sensor, a microphone, a flow meter, and/or other respiration sensing methods.

Components used in connection with generating a marked respiration waveform may be implemented within or on the patient-internal CRM 510 device, within on the patient-external xPAP 520 device, or within or on both devices. The CRM 510 and the xPAP 520 may be coupled to a remote computing device 530 such as a patient management server using a wireless or wired link. The CRM 510 may provide a first set of monitoring, diagnostic, and/or therapeutic functions to the patient. The xPAP device 520 may provide a second set of monitoring, diagnostic, and/or therapeutic functions to the patient. The CRM device 510, the xPAP device 520, or both may include sensors for sensing conditions related to patient respiration such as those identified in Table 1.

In one embodiment, the CRM device 510 may sense patient respiration. The sensed information may be transmitted to a respiration processor and/or a respiration waveform generator incorporated in the xPAP device 520 to generate the marked respiration waveform.

In another embodiment, the xPAP device 520 may sense patient respiration. Patient respiration information may be transmitted from the xPAP 520 device to the CRM device 510. The respiration information may be used by a respiration processor and/or a marked respiration waveform generator implemented within the housing of the CRM device 510 to generate the marked respiration waveform.

In yet another embodiment, CRM device 510 may sense a first set of patient conditions related to respiration and the xPAP device 520 may sense a second set of conditions related to respiration. Patient respiration information may be transmitted from the xPAP 520 device and the CRM device 510 to a remote device 530 that houses a respiration processor and/or a marked respiration waveform generator. The conditions related to respiration may be used by the patient management server 530 for generating a marked respiration waveform.

Data related to marked or unmarked respiration waveforms and/or respiration characteristics may be transmitted to a separate device, stored in memory, printed, and/or displayed on a display device 560. The display device may display the marked respiration waveform including the respiration waveform annotated with symbols indicating respiration characteristics. A displayed symbol may comprise an icon, graphic, alphanumeric character, or other marker positioned relative to the respiration waveform to indicate a time of occurrence of the particular characteristic and/or condition. The displayed symbol may indicate, for example, a numerical value or a textual description associated with the respiration characteristic, e.g., average respiration rate, expiratory slope, etc.

In one embodiment, the marked respiration waveform may comprise symbols positioned relative to the respiration waveform indicating one or more episodes of disordered breathing. Various characteristics of the disordered breathing episodes, including numerically quantifiable characteristics, such as episode duration and blood oxygen saturation, and/or other detected characteristics such as disordered breathing type may also be displayed on the display.

Disordered breathing may be identified and evaluated using various physiological and/or non-physiological (contextual) conditions. Table 2 provides examples of how a representative subset of the conditions listed in Table 1 may be used in connection with disordered breathing detection and/or evaluation. It will be appreciated that patient conditions and detection methods other than those listed in Tables 1 and 2 may be used and are considered to be within the scope of the invention.

TABLE 2

| Condition Type | Condition | Examples of how condition may be used in disordered breathing detection |
|---|---|---|
| Physiological | Heart rate | Decrease in heart rate may indicate disordered breathing episode. Increase in heart rate may indicate autonomic arousal from a disordered breathing episode. Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | $CO_2$ | Low $CO_2$ levels initiate central apnea. |
| | $O_2$ | $O_2$ desaturation occurs during severe apnea/hypopnea episodes. |

TABLE 2-continued

| Condition Type | Condition | Examples of how condition may be used in disordered breathing detection |
|---|---|---|
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/ Medication/ Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

Detection of disordered breathing may involve comparing one condition or multiple conditions to one or more thresholds or other indices indicative of disordered breathing. A threshold or other index indicative of disordered breathing may comprise a predetermined level of a particular condition, e.g., blood oxygen level less than a-predetermined amount. A threshold or other index indicative of disordered breathing may involve a change in a level of a particular condition, e.g., heart rate decreasing from a sleep rate to a lower rate within a predetermined time interval.

In one approach, the relationships between the conditions may be indicative of disordered breathing. In this embodiment, disordered breathing detection may be based on the existence and relative values associated with two or more conditions. For example, if condition A is present at a level of x, then condition B must also be present at a level of f(x) before a disordered breathing detection is made.

The thresholds and/or relationships indicative of disordered breathing may be highly patient specific. The thresholds and/or relationships indicative of disordered breathing may be determined on a case-by-case basis by monitoring conditions affecting the patient and monitoring disordered breathing episodes. The analysis may involve determining levels of the monitored conditions and/or relationships between the monitored conditions associated, e.g., statistically correlated, with disordered breathing episodes. The thresholds and/or relationships used in disordered breathing detection may be updated periodically to track changes in the patient's response to disordered breathing.

In various implementations, episodes of disordered breathing may be detected through analysis of the patient's respiration patterns. Methods and systems of disordered breathing detection based on respiration patterns are further described in commonly owned U.S. patent application Ser. No. 10/309, 770 filed Dec. 4, 2002, now U.S. Pat. No. 7,252,640, which is incorporated herein by reference.

In various embodiments, episodes of disordered breathing may be detected by monitoring the respiration waveform signal generated by a transthoracic impedance sensor. In one example, when the tidal volume (TV) of the patient's respiration, as indicated by the transthoracic impedance signal, falls below a hypopnea threshold, then a hypopnea event is declared. A hypopnea event may be declared, for example, if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 7:
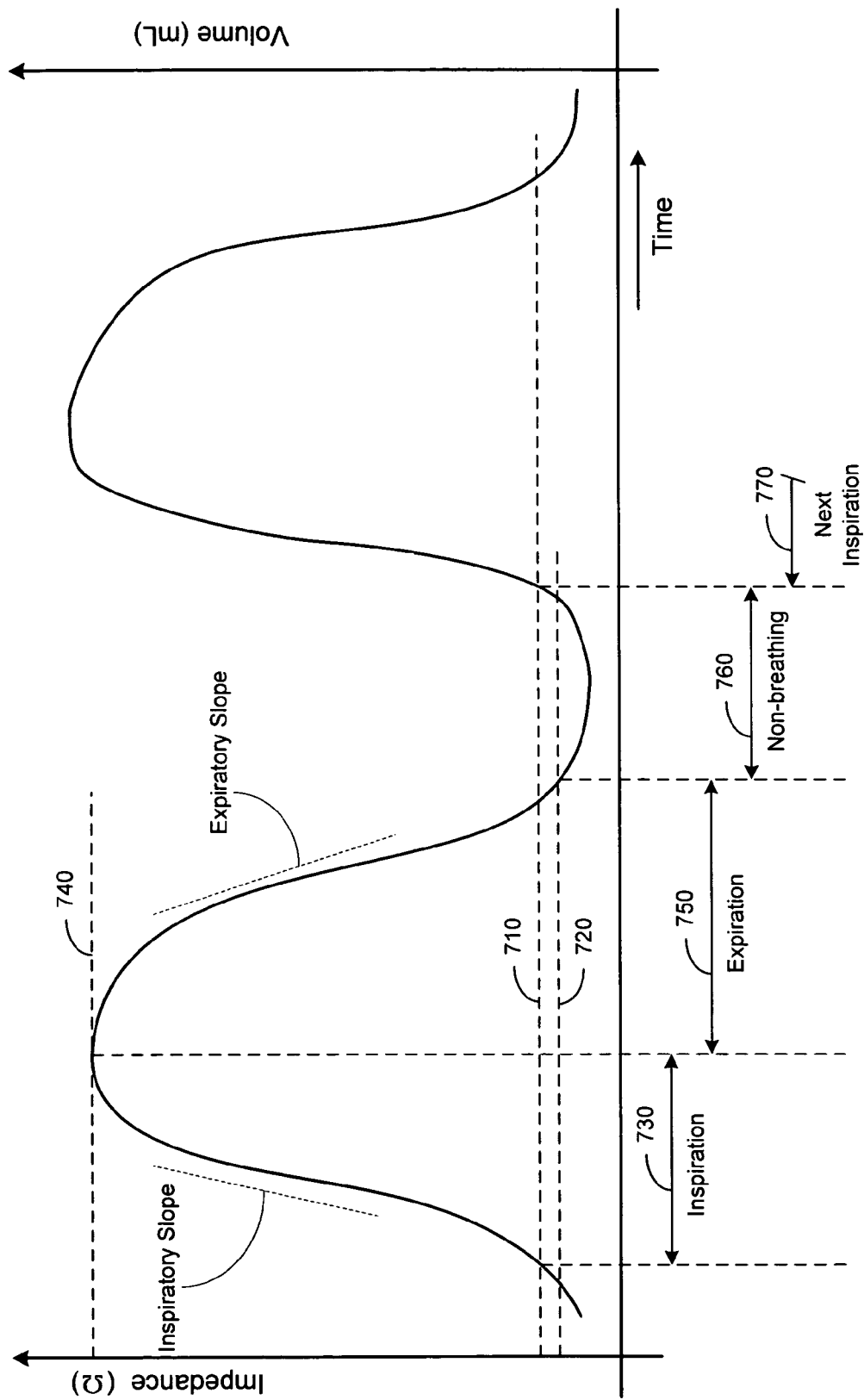
FIG. 7 is a graph illustrating respiration intervals used for characterizing patient respiration according to embodiments of the invention.

In one embodiment, detection of disordered breathing involves defining and analyzing respiratory cycle intervals. FIG. 7 is a graph illustrating respiration intervals that may be used for detecting disordered breathing according to embodiments of the invention. Respiratory intervals in a respiration cycle can be divided into an inspiration period 730 corresponding to the patient inhaling, an expiration period 750, corresponding to the patient exhaling, and a non-breathing period 760 occurring between inhaling and exhaling. Respiration intervals are established using inspiration 710 and expiration 720 thresholds. The inspiration threshold 710 marks the beginning of an inspiration period 730 and is determined by the transthoracic impedance signal rising above the inspiration threshold 710. The inspiration period 730 ends when the transthoracic impedance signal is maximum 740. A maximum transthoracic impedance signal 740 corresponds to both the end of the inspiration period 730 and the beginning of the expiration period 750. The expiration period 750 continues until the transthoracic impedance falls below an expiration threshold 720. A non-breathing period 760 starts from the end of the expiration period 750 and continues until the beginning of the next inspiration period 770.

Figure 8:
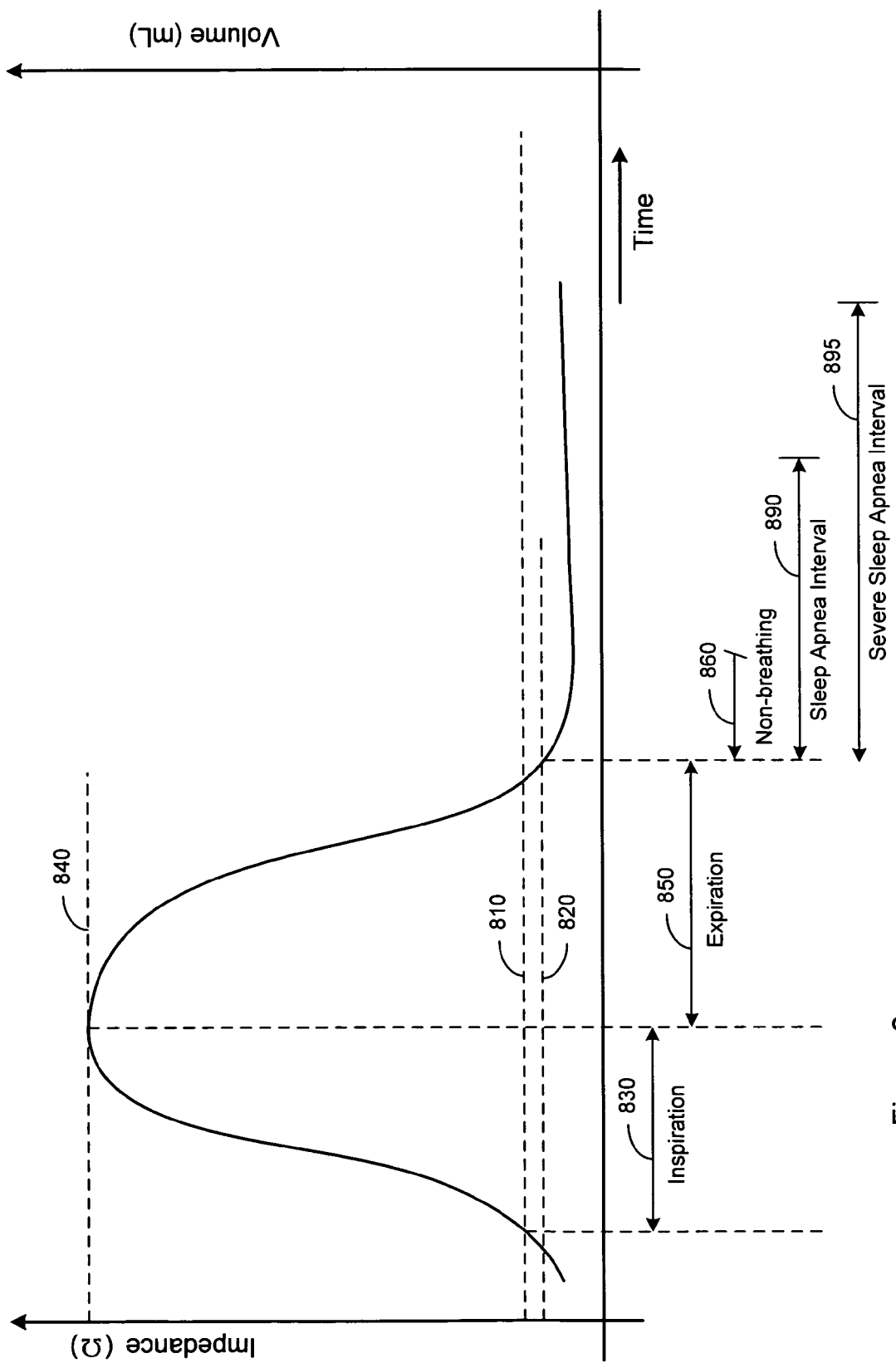
FIG. 8 is a graph illustrating respiration patterns indicative of sleep apnea and severe sleep apnea in accordance with embodiments of the invention.

Respiration patterns used for the detection of disordered breathing in the form of sleep apnea and severe sleep apnea are illustrated in FIG. 8. Patient respiration signals are monitored and the respiration cycles are defined according to inspiration 830, expiration 850, and non-breathing 860 periods as described in connection with FIG. 7. A condition of sleep apnea is detected when a non-breathing period 860 exceeds a first predetermined interval 890, denoted the sleep apnea interval. A condition of severe sleep apnea is detected when the non-breathing period 860 exceeds a second predetermined interval 895, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of disordered breathing characterized by abnormally shallow breathing. FIGS. 9A-9B are graphs of tidal volume derived from transthoracic impedance measurements. The graphs compare the tidal volume of a normal breathing cycle to the tidal volume of a hypopnea episode. FIG. 9A illustrates normal respiration tidal volume and rate. As shown in FIG. 9B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle may be derived from transthoracic impedance measurements. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold.

Figure 10:
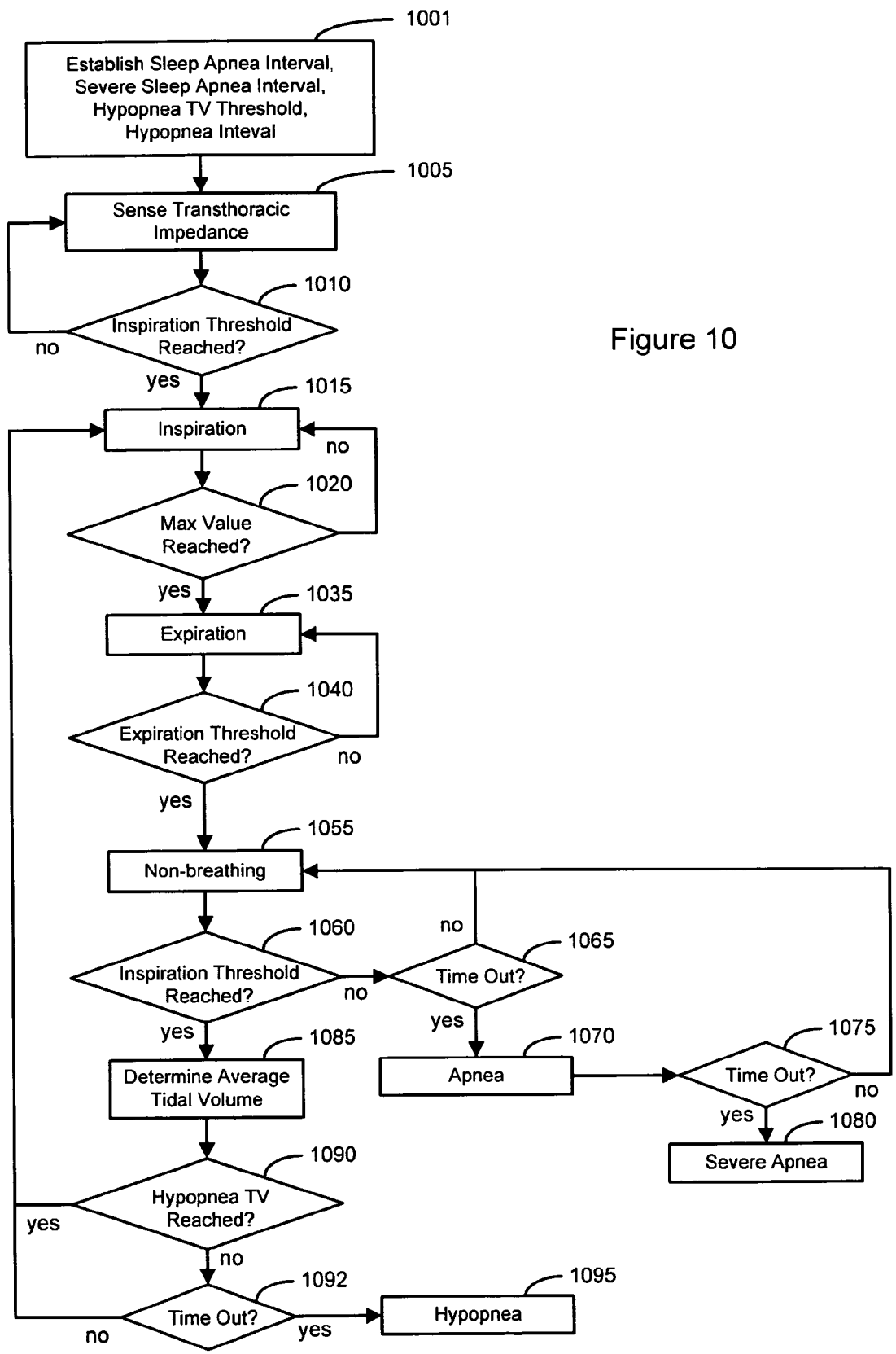
FIG. 10 is a flowchart illustrating a method of apnea and/or hypopnea detection according to embodiments of the invention.

FIG. 10 is a flow chart illustrating a method of apnea and/or hypopnea detection according to embodiments of the invention. Various thresholds or other indices associated with patient respiration are established 1001 before analyzing the patient's respiration for disordered breathing episodes. For example, inspiration and expiration thresholds, sleep apnea interval, severe sleep apnea interval, and/or a hypopnea tidal volume threshold may be established.

The patient's transthoracic impedance is sensed 1005 as described in more detail above. If the transthoracic impedance reaches or exceeds 1010 the inspiration threshold, the beginning of an inspiration interval is detected 1015. If the transthoracic impedance remains below 1010 the inspiration threshold, then the impedance signal is checked 1005 periodically until inspiration 1015 occurs.

During the inspiration interval, the patient's transthoracic impedance is monitored until a maximum value of the transthoracic impedance is detected 1020. Detection of the maximum value signals an end of the inspiration period and a beginning of an expiration period 1035.

The expiration interval is characterized by decreasing transthoracic impedance. When the transthoracic impedance falls 1040 below the expiration threshold, a non-breathing interval is detected 1055.

If the transthoracic impedance does not exceed 1060 the inspiration threshold within a first predetermined interval 1065, denoted the sleep apnea interval, then a condition of sleep apnea is detected 1070. Severe sleep apnea is detected 1080 if the non-breathing period extends beyond a second predetermined interval 1075, denoted the severe sleep apnea interval.

When the transthoracic impedance exceeds 1060 the inspiration threshold, the tidal volume from the peak-to-peak transthoracic impedance is calculated, along with a moving average of past tidal volumes 1085. The peak-to-peak transthoracic impedance provides a value proportional to the tidal volume of the respiration cycle. This value is compared to a hypopnea tidal volume threshold 1090. If the peak-to-peak transthoracic impedance is consistent with the hypopnea tidal volume threshold 1090 for a predetermined time 1092, then a hypopnea cycle is detected 1095.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 11:
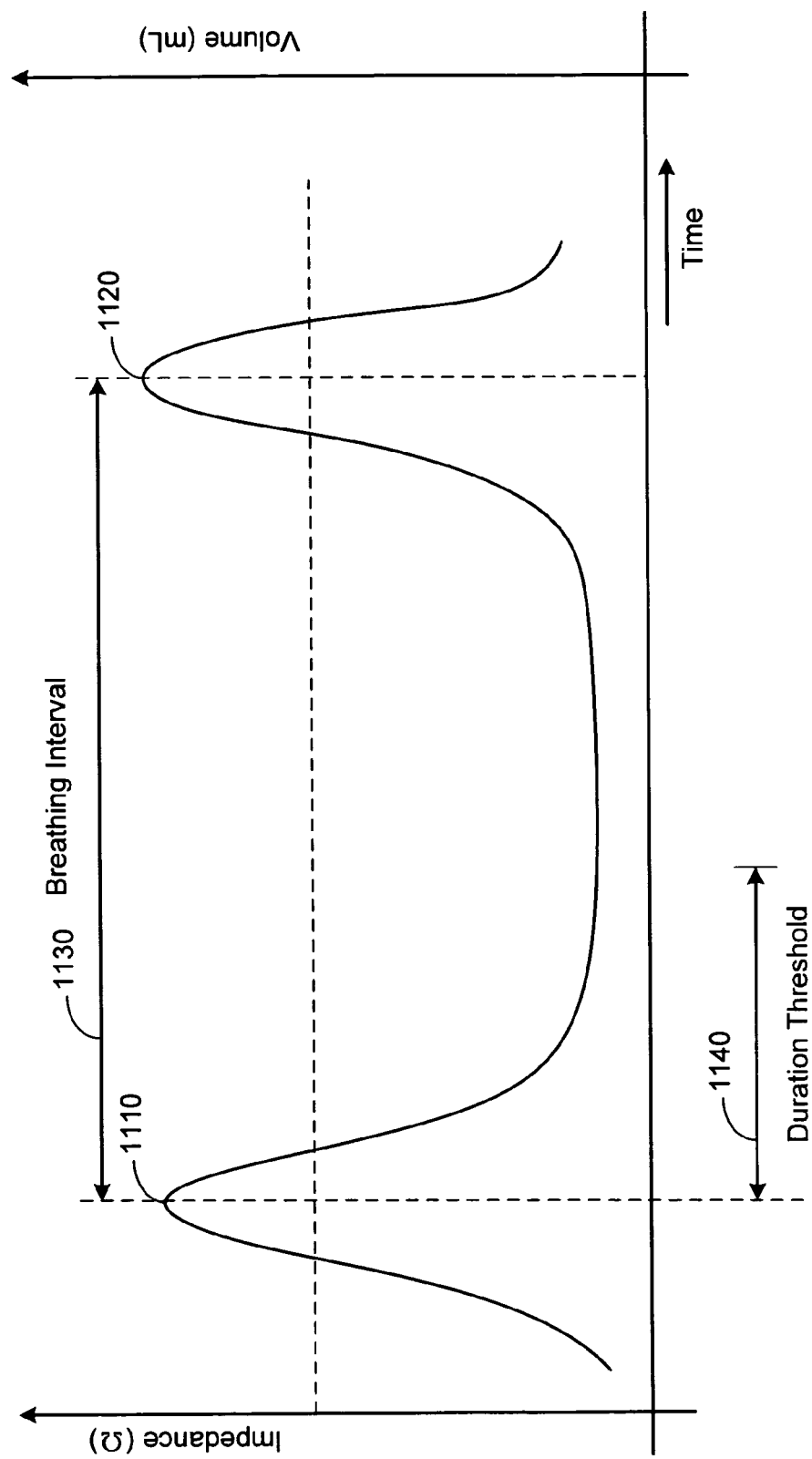
FIG. 11 is a respiration graph illustrating a breath interval utilized in connection with characterizing disordered respiration in accordance with embodiments of the invention.

According to principles of the invention, a breath interval is established for each respiration cycle. FIG. 11 is a respiration graph illustrating a breath interval utilized in connection with characterizing disordered breathing in accordance with embodiments of the invention. A breath interval represents the interval of time between successive breaths. A breath interval 1130 may be defined in a variety of ways, for example, as the interval of time between successive maxima 1110, 1120 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 11. Apnea represents a period of non-breathing. A breath interval 1130 exceeding a duration threshold 1140 comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 12:
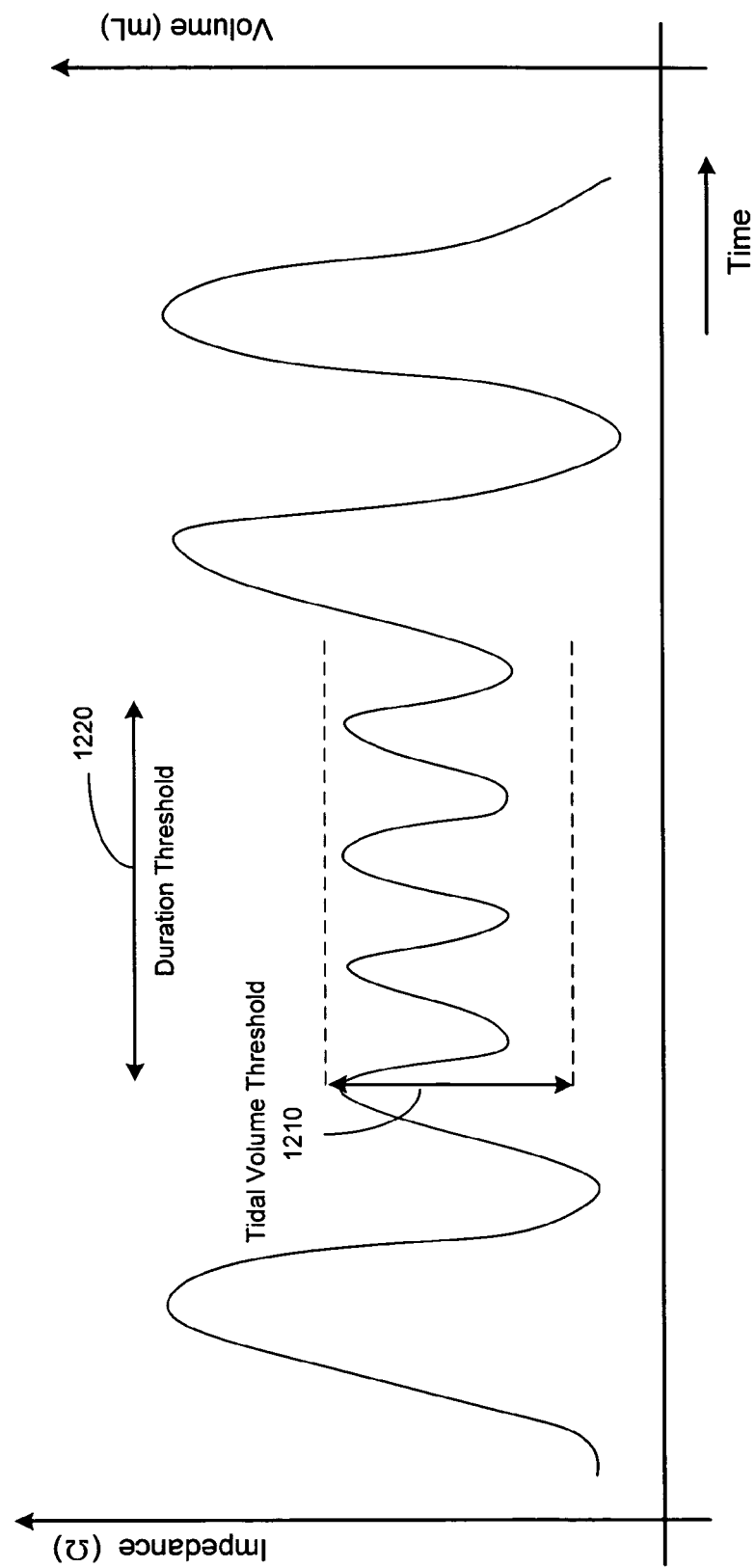
FIG. 12 is a respiration graph illustrating a hypopnea characterization approach in accordance with embodiments of the invention.

A respiration graph illustrating a hypopnea characterization approach in accordance with embodiments of the invention is illustrated in FIG. 12. Shallow breathing is detected when the tidal volume of one or more breaths is below a tidal volume threshold 1210. If the shallow breathing continues for an interval greater than a duration threshold 1220, then the breathing pattern represented by the sequence of shallow respiration cycles, is classified as a hypopnea event.

Figure 13:
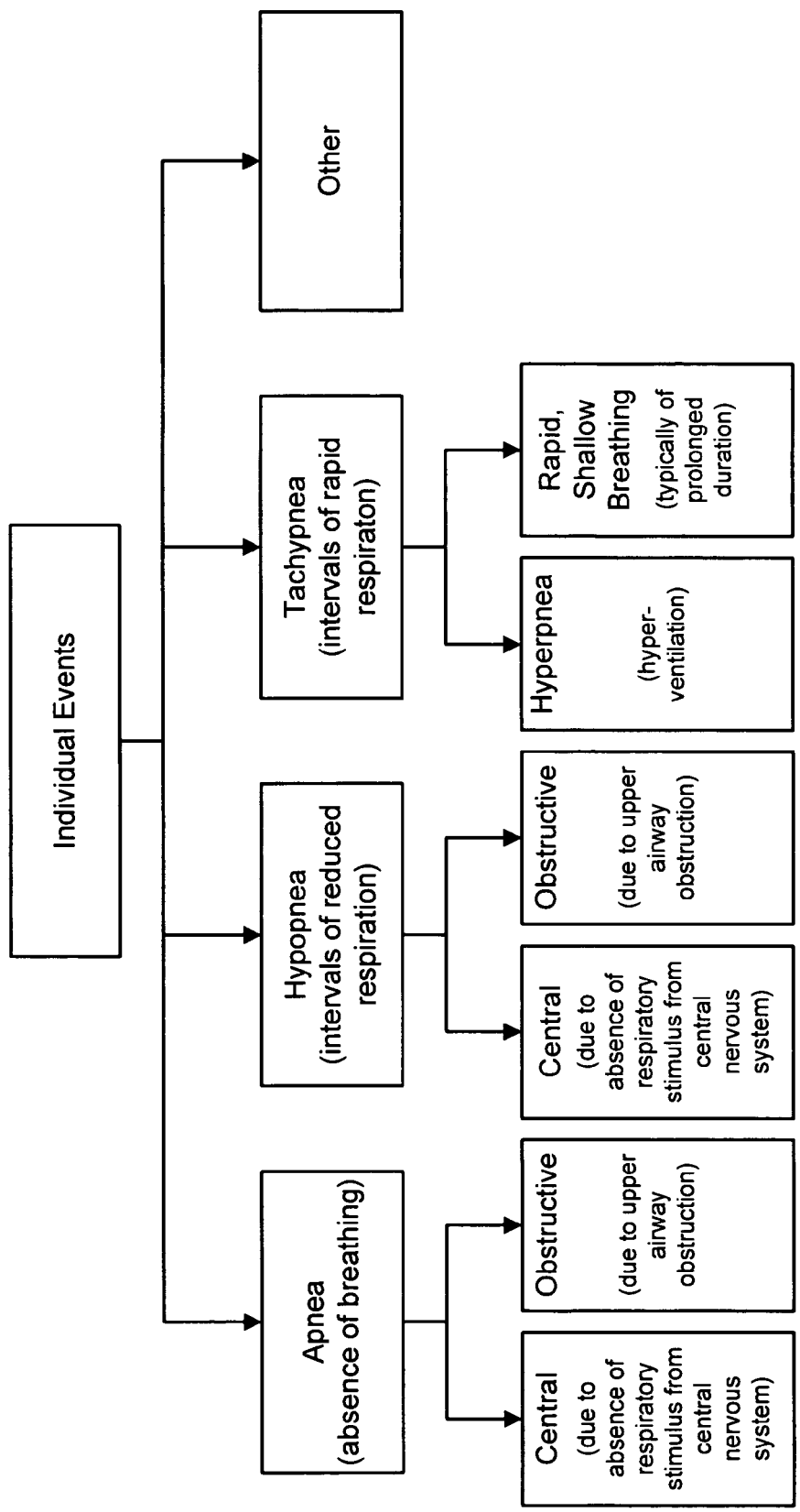
FIGS. 13 and 14 provide charts illustrating classification of individual disordered breathing events and series of periodically recurring disordered breathing events, respectively, in accordance with embodiments of the invention.
Figure 14:
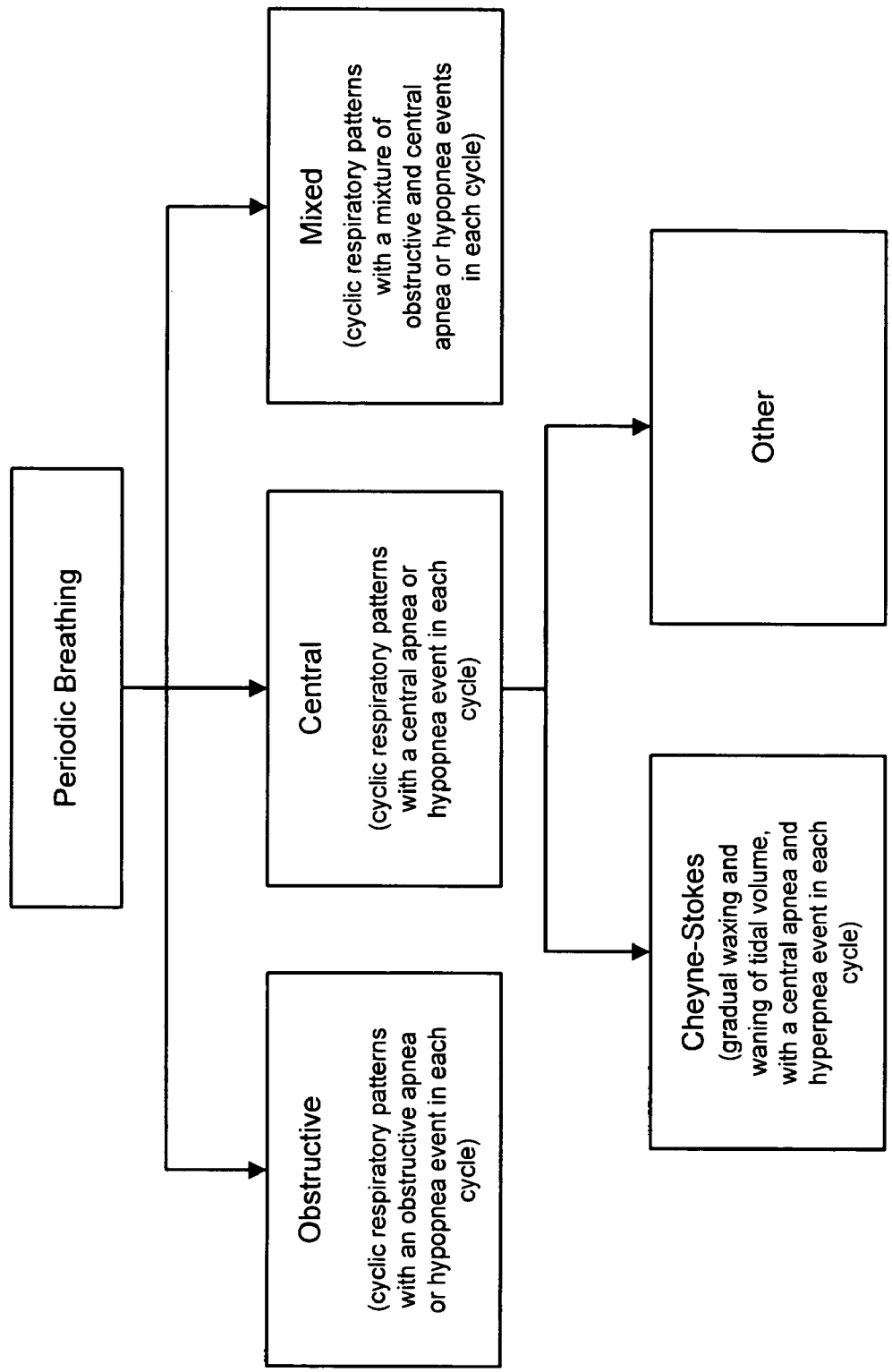

FIGS. 13 and 14 provide charts illustrating classification of individual disordered breathing events and series of periodically recurring disordered breathing events, respectively. As illustrated in FIG. 13, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 13, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 14 illustrates classification of combinations of periodically recurring disordered breathing events. Periodic breathing may be classified as being obstructive, central or mixed in origin. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle as illustrated in FIG. 15F. Cheyne-Stokes is a particular type of periodic breathing involving a gradual waxing and waning of tidal volume and having a central apnea and hyperpnea event in each cycle as illustrated in FIG. 15G. Other manifestations of periodic breathing are also possible. Disordered breathing episodes may be classified based on the characteristic respiration patterns associated with particular types of disordered breathing.

Figures 15A, 15B, 15C, 15D, 15E:
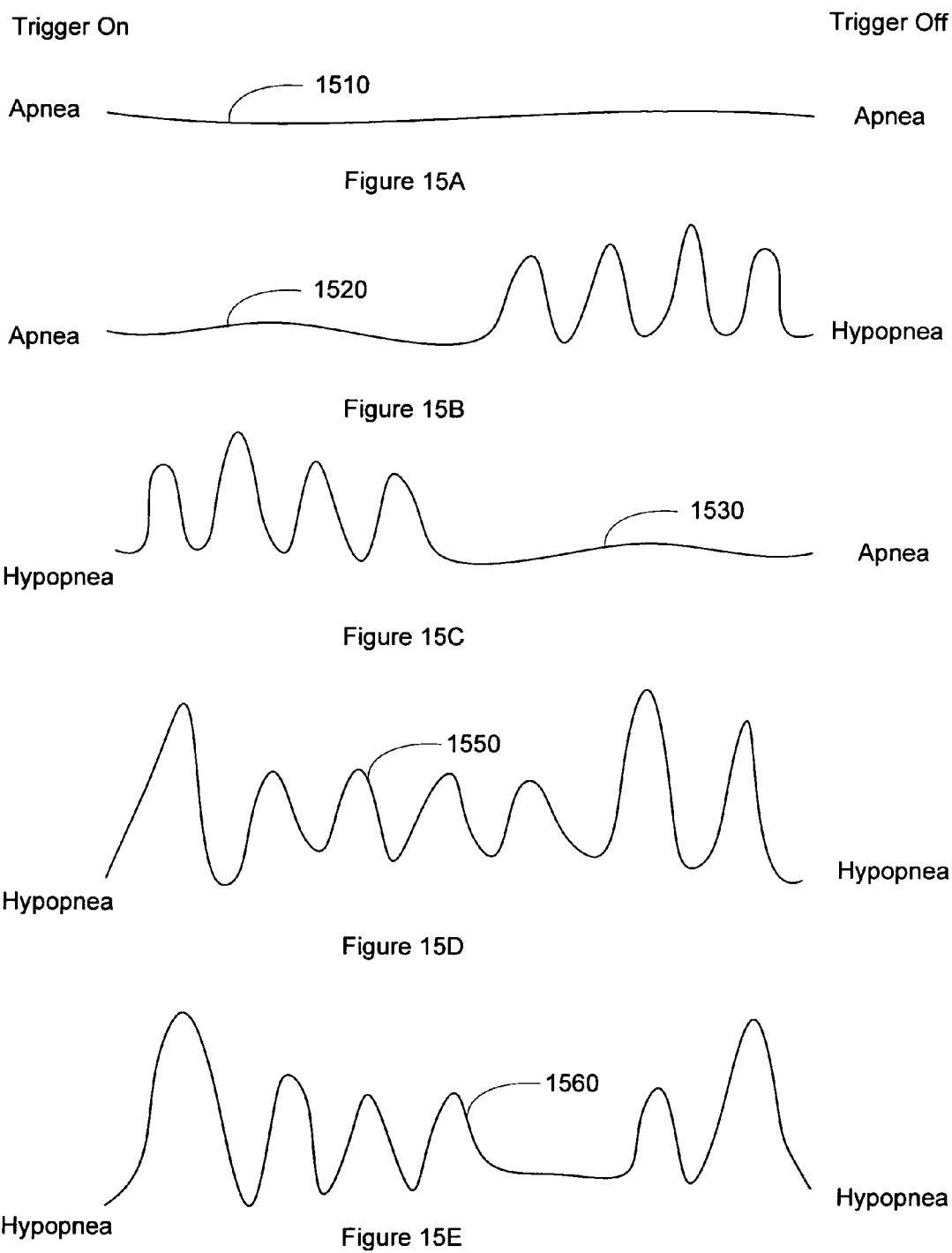
FIGS. 15A-E provide graphs illustrating respiration patterns of disordered breathing episodes that may be detected and characterized in accordance with embodiments of the invention.
Figure 15F:
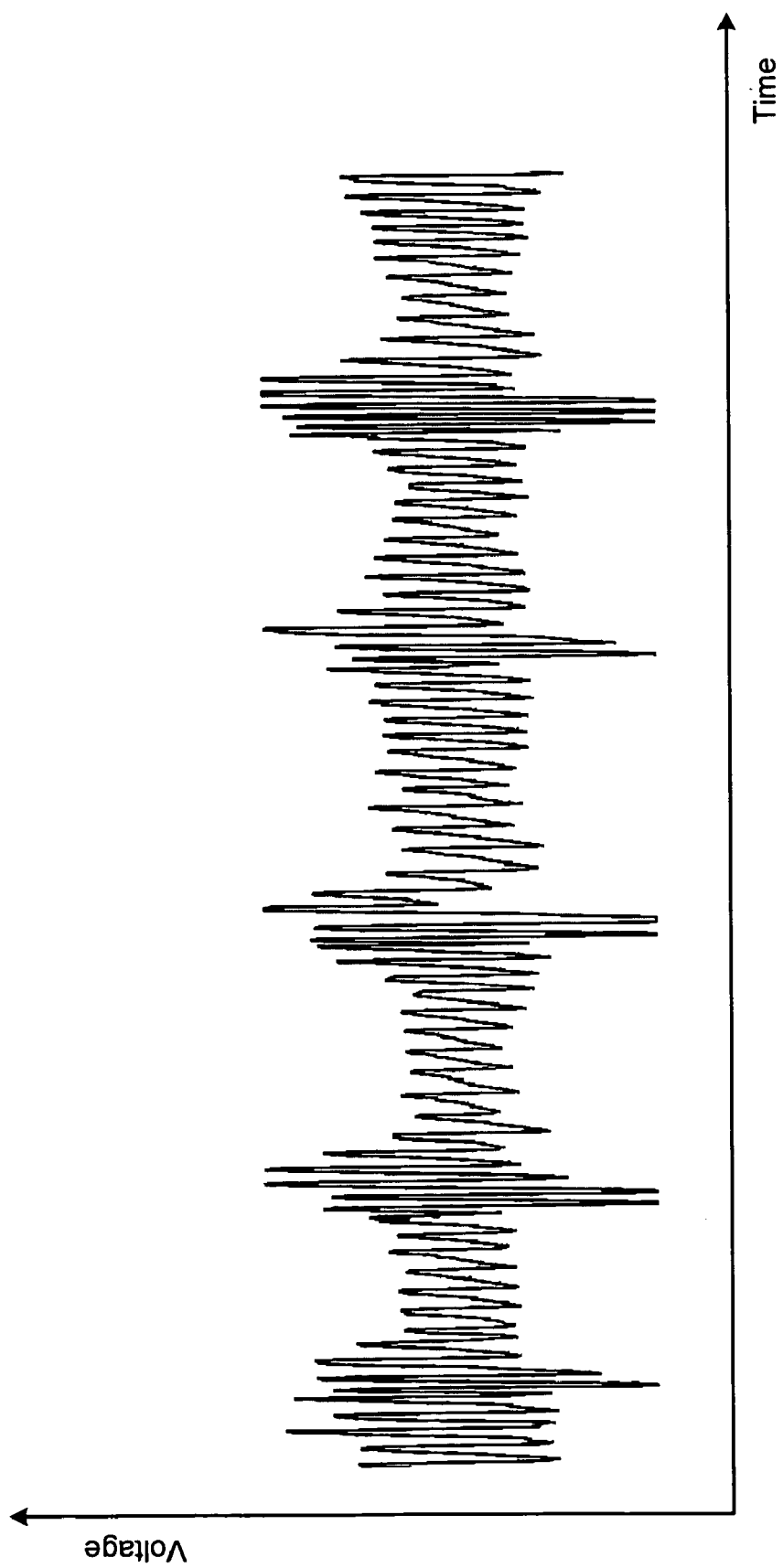
FIG. 15F is a graph illustrating a respiration pattern indicative of periodic breathing in accordance with embodiments of the invention.
Figure 15G:
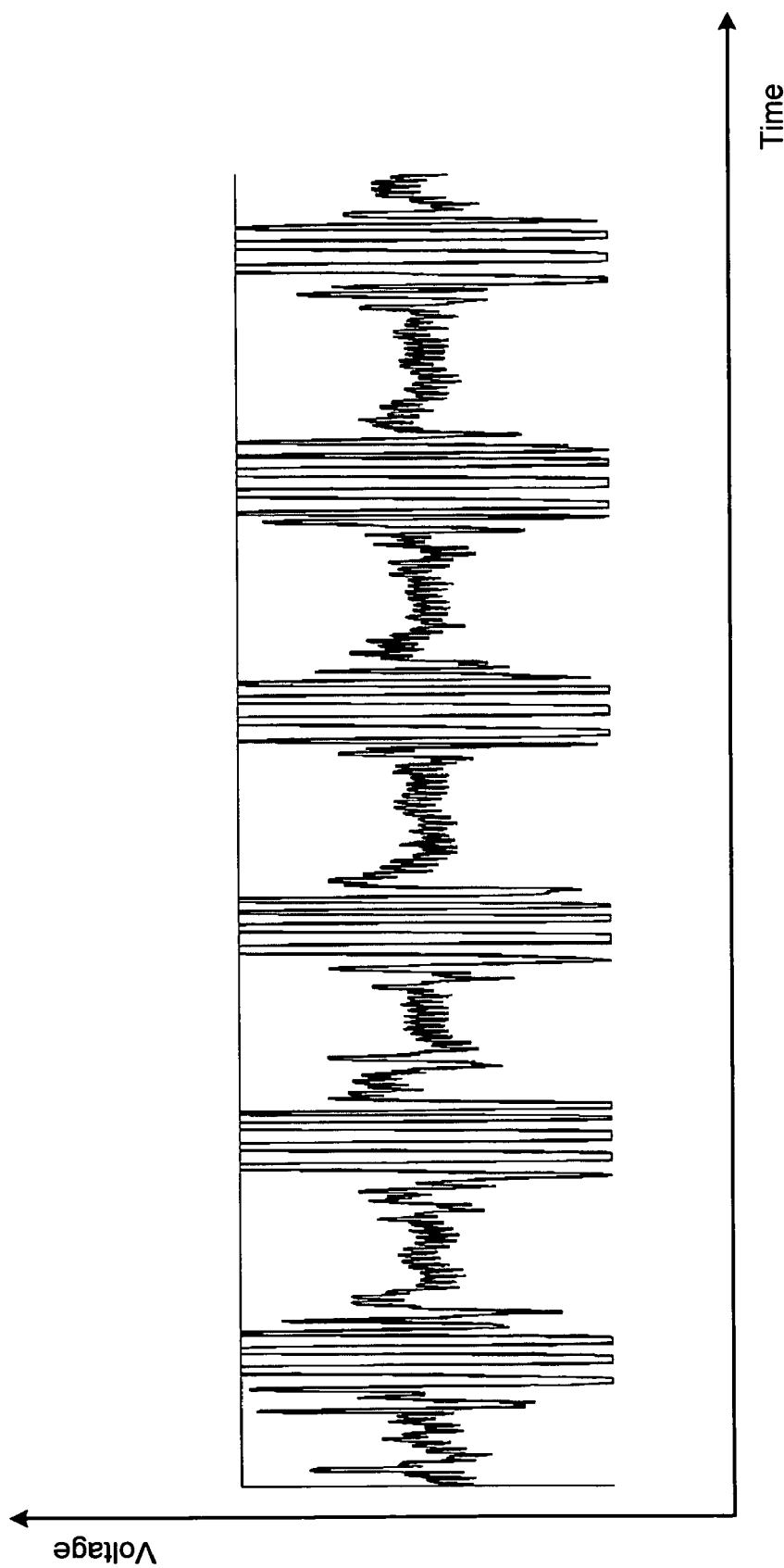
FIG. 15G is a graph illustrating a respiration pattern indicative of Cheyne-Stokes respiration in accordance with embodiments of the invention.

As illustrated in FIGS. 15A-E, a respiration pattern detected as a disordered breathing episode may include only an apnea respiration cycle 1510 (FIG. 15A), only hypopnea respiration cycles 1550 (FIG. 15D), or a mixture of hypopnea and apnea respiration cycles 1520 (FIG. 15B), 1530 (FIG. 15C), 1560 (FIG. 15E). A disordered breathing event 1520 may begin with an apnea respiration cycle and end with one or more hypopnea cycles. In another pattern, the disordered breathing event 1530 may begin with hypopnea cycles and end with an apnea cycle. In yet another pattern, a disordered breathing event 1560 may begin and end with hypopnea cycles with an apnea cycle in between the hypopnea cycles.

Disordered breathing events may be classified as either central disordered breathing, obstructive disordered breathing, or a combination of central and obstructive types. In accordance with embodiments of the invention, symbols indicating the detection of central or obstructive disordered breathing events may be included in a marked respiration waveform.

Central disordered breathing events are characterized by insufficient respiration and a concurrent lack of respiratory effort. Because the central nervous system signals that control breathing are interrupted, the patient's natural breathing reflex is not triggered. The patient makes no effort to breath or the respiratory effort is otherwise disrupted. Respiration ceases or is insufficient during the disordered breathing event.

An obstructive disordered breathing event may occur due to an obstruction of a patient's airway. For example, the patient's tongue or other soft tissue of the throat may collapse into the patient's airway. The breathing reflex is triggered, but respiration is disrupted because of the occluded airway. Disordered breathing events may include central disordered breathing events, obstructive disordered breathing events, or mixed disordered breathing events that are a combination of obstructive and central types.

Classifying disordered breathing events as central, obstructive, or a combination of central and obstructive allows physicians to more accurately diagnose and treat disordered breathing. One method for classifying a disordered breathing event as central or obstructive involves detecting disordered breathing and detecting motion associated with respiratory effort. Respiratory effort may be detected, for example, based on chest wall motion and/or abdominal motion associated with respiratory effort. Disordered breathing may be detected based on the patient's respiration patterns, or by other methods described herein. The disordered breathing event may be further classified as a central, obstructive or mixed type based on the patient's respiratory efforts during disordered breathing event.

Figure 16A:
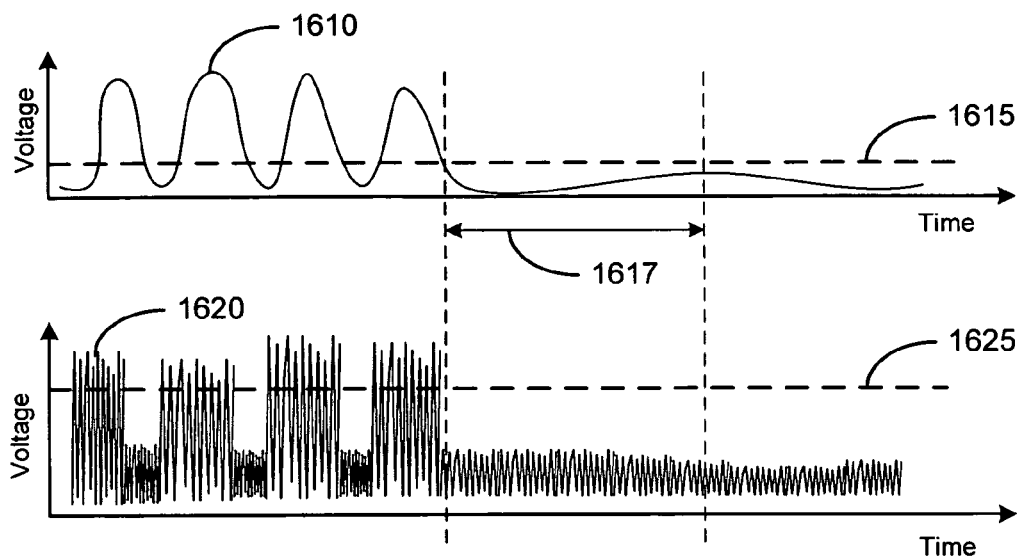
FIGS. 16A and 16B are graphs of representative accelerometer signals associated with chest wall motion for central and obstructive disordered breathing events, respectively, in accordance with embodiments of the invention.
Figure 16B:
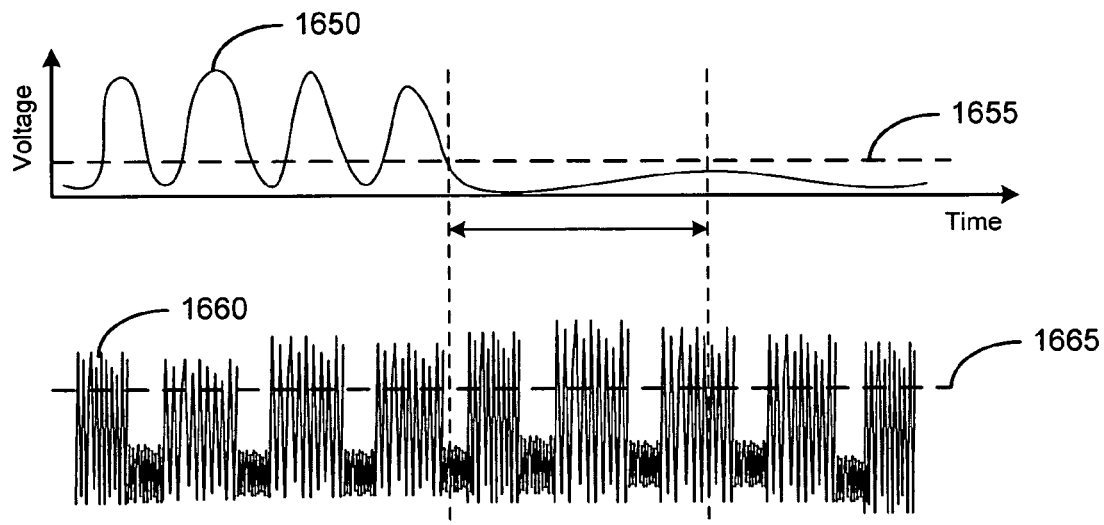

In accordance with various embodiments of the invention a disordered breathing event may be classified as central disordered breathing or obstructive disordered breathing based on chest wall motions associated with respiratory effort. FIGS. 16A and 16B are graphs of representative accelerometer signals associated with chest wall motion for central and obstructive disordered breathing, respectively. As illustrated in FIG. 16A, apnea is detected when the transthoracic impedance signal 1610 remains below an inspiration threshold 1615 for a period of time greater than an apnea interval 1617, e.g., about 10 seconds. In this example, the apnea event is a central apnea event and the signal 1620 from an accelerometer sensing the patient's chest wall motion also falls below a motion threshold 1625 during the period of non-respiration. The lack of chest wall motion indicates that the patient's breathing reflex is not being triggered by the central nervous system, indicative of central disordered breathing.

FIG. 16B illustrates the accelerometer signal and transthoracic impedance signal during obstructive apnea. Apnea is detected when the transthoracic impedance signal 1650 remains below an inspiration threshold 1655 for a period of time greater than an apnea interval 1657. In this example, the apnea is obstructive apnea and the signal 1660 from an accelerometer sensing the patient's chest wall motion rises above a chest well motion threshold 1665 during the period of non-respiration. The chest wall motion indicates that the patient's breathing reflex is being triggered by the central nervous system, indicative of obstructive disordered breathing. One or more symbols indicating the detection of central or obstructive disordered breathing may be included in a marked respiration waveform.

FIG. 17A illustrates a marked respiration waveform in accordance with embodiments of the invention. In one embodiment, information related to a marked respiration waveform may be acquired continuously as a moving snapshot of respiration-related conditions. In another embodiment, the information related to the marked respiration waveform may be acquired in response to one or more triggering events. In one example, the triggering event may comprise an instruction from a physician or an automatically generated instruction provided by an advanced patient management system to begin data collection. In another example, the triggering event may comprise detection of various respiration conditions, such as detection of the disordered breathing, the detection of sleep, or the detection of a particular pulmonary condition. In this scenario, the triggering event may initiate the collection of respiration-related data during an interval of time that may include time periods prior to, during, and/or following the disordered breathing event.

As illustrated in FIG. 17A, the marked respiration waveform 1710 may comprise respiratory symbols positioned at locations relative to the respiration waveform to indicate the time of occurrence of respiration events, and the time of occurrence of various respiration conditions and/or characteristics. In the example depicted in FIG. 17A, the respiration waveform 1710 is marked with minute ventilation symbols 1720 denoting peaks on the waveform and apnea markers 1730,1735 denoting when an apnea event is detected 1730 and when the apnea event ends 1735. In addition, other symbols indicating respiration characteristics and/or disordered breathing characteristics described above may be used to annotate the respiration waveform. The marked respiration waveform information may be stored, transmitted, printed and/or displayed on a display device to allow the patient's physician to view respiratory disturbances and/or other characteristics. Generation of a marked respiration waveform allows a clinician to view respiration disturbances and to determine that respiration events were properly detected. Further, the marked respiration waveform may be used to guide diagnosis and therapy.

Figure 17B:
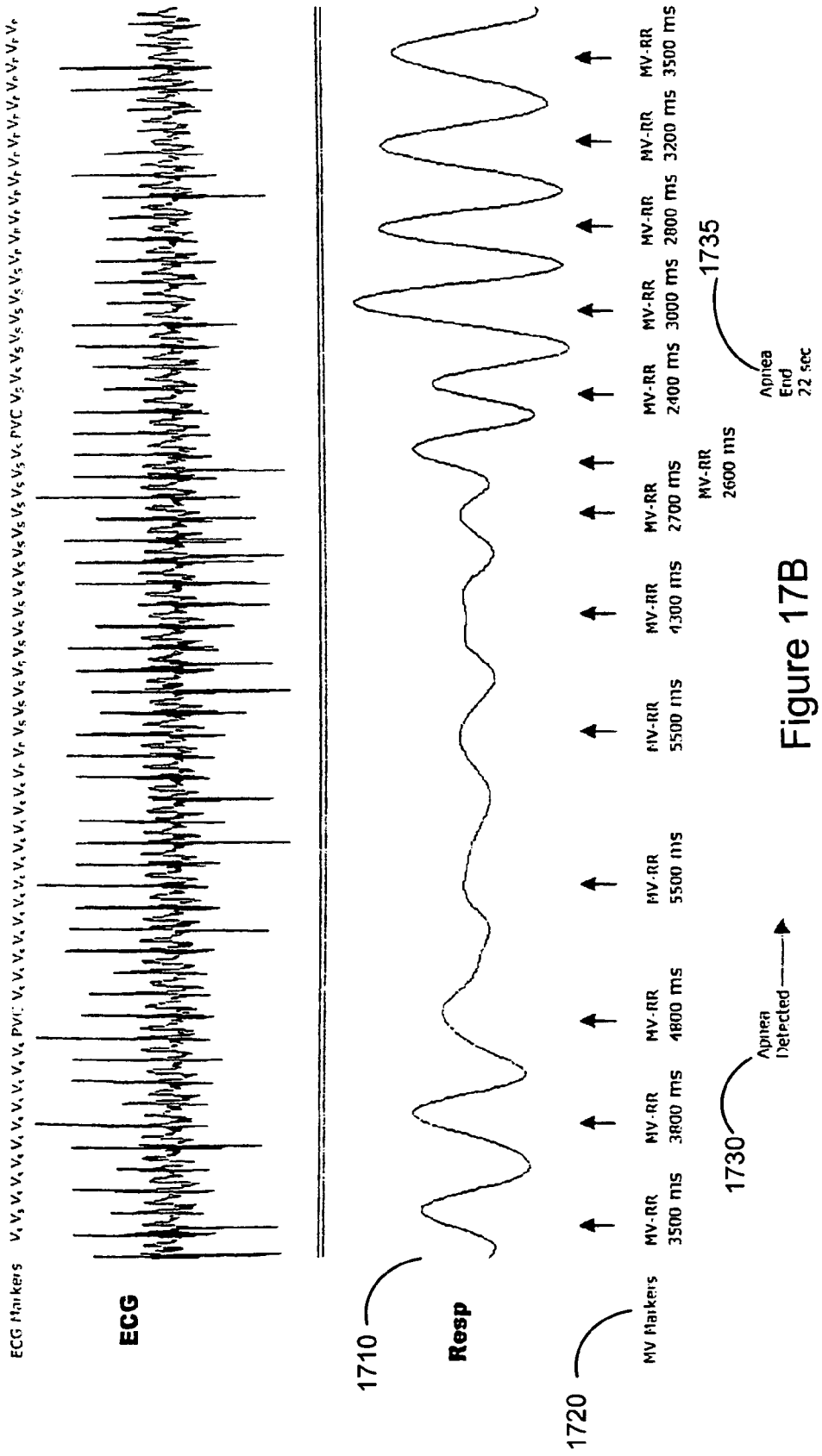
FIG. 17B illustrates a marked respiration waveform including respiration and ECG graphs in accordance with embodiments of the invention.

FIG. 17B provides an illustration of a marked respiration waveform in accordance with embodiments of the invention including respiration and electrocardiogram (ECG) graphs. The respiration waveform and ECG graph, such as the one depicted in FIG. 17B, may be produced, for example, by a medical device having a transthoracic impedance sensor and intracardiac EGM electrodes.

As illustrated in FIG. 17B, the marked respiration waveform may present one or more additional waveforms. The additional waveforms may include, for example, waveforms depicting patient activity, posture, blood gas, blood pressure, and/or other waveforms. In FIG. 17B, an ECG is shown above respiratory waveform 1710. The ECG is time-aligned with respiration waveform 1710 and can be marked with indicators corresponding to the occurrence of breathing events, cardiac events, and/or other events. Displaying marked respiration waveforms and other waveforms related to patient conditions allows the patient's physician to verify, for example, that a disordered breathing event was properly detected. This confirmation may be used to enhance diagnosis and/or therapy. Symbols indicating characteristics and/or conditions related to the cardiovascular, respiratory and/or other physiological systems provide further diagnostic information for physicians. For example, annotated waveforms allow a physician to evaluate the impact of respiration events on other physiological systems.

As previously mentioned, changes in various respiration-related conditions occur or are more likely to occur during sleep. For example, episodes of disordered breathing can occur when the patient is awake, however, disordered breathing most frequently occurs during sleep. The onset and termination or sleep, sleep stages and/or sleep quality characteristics may be indicated or otherwise used in the generation of marked respiratory waveform. Methods and systems for detecting sleep, aspects of which may be utilized in the generation of a marked respiration waveform, are described in commonly owned U.S. patent application Ser. No. 10/309,771, filed Dec. 4, 2002, now U.S. Pat. No. 7,189,204, which is incorporated by reference. Methods and systems for detecting REM sleep and/or other sleep states are described in commonly owned U.S. patent application Ser. No. 10/643,006, filed Aug. 18, 2003, now U.S. Publication No. 2005/0043652, which is incorporated by reference. Methods and systems for evaluation of sleep quality characteristics which may be used to generate a marked respiratory waveform are described in commonly owned patent application Ser. No. 10/642,998, filed Aug. 18, 2003, now U.S. Publication No. 2005/0042589, which is incorporated by reference.

Prediction of disordered breathing may trigger the generation of a marked respiration waveform. Further, symbols indicating a prediction of disordered breathing and/or other physiological events may be used to annotate the marked respiration waveform of the present invention. Disordered breathing prediction methods and systems, aspects of which may be utilized in connection with generating a marked respiration waveform, are described in commonly owned U.S. patent application Ser. No. 10/643,016, filed Aug. 18, 2003, now U.S. Pat. No. 7,396,333, which is incorporated herein by reference.

A number of the examples presented herein involve block diagrams illustrating functional blocks used for implementing marked respiration waveform generation in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed herein without departing from the scope of the present invention. Accordingly, the scope of the present invention should not be limited by the particular embodiments described above, but should be defined only by the claims set forth below and equivalents thereof.

What is claimed is:

1. A system for characterizing respiration of a patient, comprising:
    a respiration waveform sensor configured to acquire a respiration waveform;
    a respiration processor configured to determine one or more characteristics associated with the respiration and comprising a trigger circuit configured to detect a triggering event, the one or more characteristics including a first respiration characteristic and a second respiration characteristic different from the first respiration characteristic; and
    a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;
    wherein at least one of the respiration waveform sensor, the respiration processor, and the waveform generator comprises an implantable component; and
    wherein the respiration processor is further configured to distinguish between different types of disordered breathing, and the first respiration characteristic comprises a type of disordered breathing selected from the different types of disordered breathing.

2. The system of claim 1, wherein the type of the disordered breathing comprises central disordered breathing.

3. The system of claim 1, wherein the type of the disordered breathing comprises obstructive disordered breathing.

4. The system of claim 1, wherein the type of the disordered breathing comprises mixed central and obstructive disordered breathing.

5. The system of claim 1, wherein the type of the disordered breathing comprises apnea.

6. The system of claim 1, wherein the type of the disordered breathing comprises hypopnea.

7. The system of claim 1, wherein the type of the disordered breathing comprises mixed apnea and hypopnea.

8. The system of claim 1, wherein the type of the disordered breathing comprises Cheyne-Stokes respiration.

9. The system of claim 1, wherein the type of the disordered breathing comprises periodic breathing.

10. The system of claim 1, wherein the type of the disordered breathing comprises sleep disordered breathing.

11. A system for characterizing respiration of a patient, comprising:
    a respiration waveform sensor configured to acquire a respiration waveform;
    a respiration processor configured to determine one or more characteristics associated with the respiration and comprising a trigger circuit configured to detect a triggering event, the one or more characteristics including a first respiration characteristic and a second respiration characteristic different from the first respiration characteristic; and
    a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;

wherein at least one of the respiration waveform sensor, the respiration processor, and the waveform generator comprises an implantable component; and wherein the one or more characteristics associated with the respiration comprises a respiration volume.

12. A system for characterizing respiration of a patient, comprising:

a respiration waveform sensor configured to acquire a respiration waveform;

a respiration processor configured to determine one or more characteristics associated with the respiration and comprising a trigger circuit configured to detect a triggering event, the one or more characteristics including a first respiration characteristic and a second respiration characteristic different from the first respiration characteristic; and a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;

wherein at least one of the respiration waveform sensor, the respiration processor, and the waveform generator comprises an implantable component; and wherein the one or more characteristics associated with the respiration comprises minute ventilation.

13. A system for characterizing respiration of a patient, comprising:

a respiration waveform sensor configured to acquire a respiration waveform;

a respiration processor configured to determine one or more characteristics associated with the respiration and comprising a trigger circuit configured to detect a triggering event, the one or more characteristics including a first respiration characteristic and a second respiration characteristic different from the first respiration characteristic; and a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;

wherein at least one of the respiration waveform sensor, the respiration processor, and the waveform generator comprises an implantable component; and wherein the one or more characteristics associated with the respiration comprises expiration slope.

14. A system for characterizing respiration of a patient, comprising:

a respiration waveform sensor configured to acquire a respiration waveform;

a respiration processor configured to determine one or more characteristics associated with the respiration and comprising a trigger circuit configured to detect a triggering event, the one or more characteristics including a first respiration characteristic and a second respiration characteristic different from the first respiration characteristic; and a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;

wherein at least one of the respiration waveform sensor, the respiration processor, and the waveform generator comprises an implantable component; and wherein the one or more characteristics associated with the respiration comprises expiration volume.

15. A system for characterizing respiration of a patient, comprising:

a respiration waveform sensor configured to acquire a respiration waveform;

a respiration processor configured to determine one or more characteristics associated with the respiration and comprising a trigger circuit configured to detect a triggering event, the one or more characteristics including a first respiration characteristic and a second respiration characteristic different from the first respiration characteristic; and a waveform generator coupled to the respiration waveform sensor and the respiration processor, the waveform generator configured to generate a marked respiration waveform comprising the respiration waveform and symbols indicating the one or more characteristics associated with the respiration, the generation of the marked respiration waveform being activated in response to the detection of the triggering event, and the symbols including a first symbol indicating the first respiration characteristic and a second symbol indicating the second respiration characteristic, the first and second symbols being aligned relative to the respiration waveform to indicate times of occurrence of the first and second respiration characteristics respectively;

wherein at least one of the respiration waveform sensor, the respiration processor, and the waveform generator comprises an implantable component; and wherein the respiration processor is configured to detect the one or more characteristics associated with the respiration based on morphological features of the respiratory waveform.

* * * * *